US009717687B2

(12) United States Patent
Harashima et al.

(10) Patent No.: US 9,717,687 B2
(45) Date of Patent: Aug. 1, 2017

(54) LIPID MEMBRANE STRUCTURE INCLUDING BACTERIAL CELL COMPONENT HAVING DISPERSIBILITY IN NON-POLAR SOLVENT, AND METHOD FOR PRODUCING SAME

(71) Applicants: NATIONAL UNIVERSITY CORPORATION HOKKAIDO UNIVERSITY, Hokkaido (JP); THE UNIVERSITY OF TOKYO, Tokyo (JP); UNIVERSITY OF TSUKUBA, Ibaraki (JP); JAPAN BCG LABORATORY, Tokyo (JP)

(72) Inventors: Hideyoshi Harashima, Sapporo (JP); Takashi Nakamura, Sapporo (JP); Masafumi Fukiage, Sapporo (JP); Megumi Higuchi, Sapporo (JP); Hideyuki Akaza, Tokyo (JP); Jun Miyazaki, Tsukuba (JP); Akihiro Nakaya, Kiyose (JP)

(73) Assignees: National University Corporation Hokkaido University, Hokkaido (JP); Japan BCG Laboratory, Tokyo (JP); University of Tsukuba, Ibaraki (JP)

( * ) Notice: Subject to any disclaimer, the term of this patent is extended or adjusted under 35 U.S.C. 154(b) by 199 days.

(21) Appl. No.: 14/425,211

(22) PCT Filed: Aug. 27, 2013

(86) PCT No.: PCT/JP2013/072885

§ 371 (c)(1),
(2) Date: Mar. 2, 2015

(87) PCT Pub. No.: WO2014/034669

PCT Pub. Date: Mar. 6, 2014

(65) Prior Publication Data

US 2015/0245997 A1 Sep. 3, 2015

(30) Foreign Application Priority Data

Aug. 28, 2012 (JP) ................................ 2012-188129

(51) Int. Cl.

| | |
|---|---|
| ***A61K 9/127*** | (2006.01) |
| ***A61K 35/74*** | (2015.01) |
| ***A61K 9/50*** | (2006.01) |
| *C07K 7/06* | (2006.01) |

(52) U.S. Cl.
CPC .......... *A61K 9/1278* (2013.01); *A61K 9/1271* (2013.01); *A61K 9/1275* (2013.01); *A61K 9/5068* (2013.01); *A61K 35/74* (2013.01); *C07K 7/06* (2013.01)

(58) Field of Classification Search
None
See application file for complete search history.

(56) References Cited

U.S. PATENT DOCUMENTS

| | | | |
|---|---|---|---|
| 4,877,561 | A | 10/1989 | Iga et al. |
| 7,534,443 | B1 | 5/2009 | Azuma et al. |
| 2003/0138481 | A1 | 7/2003 | Zadi |
| 2010/0166840 | A1 | 7/2010 | Atthachai et al. |
| 2013/0149376 | A1 | 6/2013 | Ruiz et al. |

FOREIGN PATENT DOCUMENTS

| | | |
|---|---|---|
| JP | 63-039810 | 2/1988 |
| JP | 06-080560 | 3/1994 |
| JP | 2003-521508 A | 7/2003 |
| WO | WO 00/03724 | 1/2000 |
| WO | WO 2007/132790 A1 | 11/2007 |
| WO | WO 2012/003814 A1 | 1/2012 |

OTHER PUBLICATIONS

Joraku et al. BJU International 103: 686-693, published online Nov. 25, 2008.*
A. Homhuan et al., J. Controlled Release, 120:60-69 (2007).
PCT/JP2013/072885 International Search Report issued by Japanese Patent Office Nov. 26, 2013.

* cited by examiner

*Primary Examiner* — S. Devi
(74) *Attorney, Agent, or Firm* — RatnerPrestia

(57) ABSTRACT

[Problem] To provide: a lipid membrane structure which has such a particle diameter that the lipid membrane structure can be sterilized by filtration, contains a lipid that is bound to a peptide composed of multiple arginine residues as a constituent lipid, and includes a bacterial cell component having dispersibility in a non-polar solvent; and a method for producing a lipid membrane structure which has such a particle diameter that the lipid membrane structure can be sterilized by filtration and includes a substance of interest having dispersibility in a non-polar solvent.
[Solution] A lipid membrane structure which has such a particle diameter that the lipid membrane structure can be sterilized by filtration, contains a lipid that is bound to a peptide composed of multiple arginine residues as a constituent lipid, and includes a bacterial cell component having dispersibility in a non-polar solvent.

6 Claims, 18 Drawing Sheets

HBS Ethanol Pentane

BCG-CWS/HBS

Liposome encapsulating BCG-CWS/HBS

| | | Mouse a | Mouse b | Mouse c | Mouse d |
|---|---|---|---|---|---|
| The number of leukocytes / HPF | Macrophage | 7.6 | 48.2 | 58.8 | 50.6 |
| | Lymphocyte | 5.0 | 46.0 | 65.6 | 31.4 |
| | Neutrophil | 2.0 | 8.6 | 18.4 | 8.4 |
| | Eosinophil | 2.0 | 6.6 | 10.0 | 5.2 |
| | Basophil | 0.0 | 0.0 | 0.0 | 0.0 |
| | Mast cell | 1.4 | 4.0 | 5.8 | 3.8 |
| | Total number of leukocytes / HPF | 18.0 | 113.0 | 159.0 | 99.0 |
| Ratio of each cell (%) | Macrophage | 42.2 | 42.5 | 37.1 | 50.9 |
| | Lymphocyte | 27.8 | 40.6 | 41.4 | 31.6 |
| | Neutrophil | 11.1 | 7.6 | 11.6 | 8.5 |
| | Eosinophil | 11.1 | 5.8 | 6.3 | 5.2 |
| | Basophil | 0.0 | 0.0 | 0.0 | 0.0 |
| | Mast cell | 7.8 | 3.5 | 3.7 | 3.8 |
| | Total | 100 | 100 | 100 | 100 |

Environment to induce differentiation into Th1

Environment to induce differentiation into Th2

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Octa-arginine peptide (R8)

<400> SEQUENCE: 1

Arg Arg Arg Arg Arg Arg Arg Arg
1               5
```

LIPID MEMBRANE STRUCTURE INCLUDING BACTERIAL CELL COMPONENT HAVING DISPERSIBILITY IN NON-POLAR SOLVENT, AND METHOD FOR PRODUCING SAME

CROSS-REFERENCE TO RELATED APPLICATIONS

This application is a U.S. National Phase Application of PCT International Application PCT/JP2013/072885, filed Aug. 27, 2013 which claims priority to Japanese Application No. 2012-188129, filed Aug. 28, 2012, the contents of which are incorporated herein by reference in their entireties for all purposes.

TECHNICAL FIELD

The present invention relates to a lipid membrane structure encapsulating a bacterial cell component having dispersibility in a non-polar solvent, and a method for producing the same. More specifically, the present invention relates to a lipid membrane structure having a particle size that permits filtration sterilization, comprising a lipid bound with a peptide consisting of a plurality of arginine residues as a constituent lipid and encapsulating a bacterial cell component having dispersibility in a non-polar solvent, and a method for producing a lipid membrane structure having a particle size that permits filtration sterilization and encapsulating a substance of interest having dispersibility in a non-polar solvent.

BACKGROUND OF THE INVENTION

Various carriers have been developed in order to deliver substances of interest such as drugs to cells. Particularly, when the substances of interest are bacterial cell components such as a cell-wall skeleton (CWS) fraction of *Mycobacterium Bovis bacillus* Calmette-Guerin (BCG), strong immunostimulatory activity is expected. These bacterial cell components, however, are insoluble in water and are therefore difficult to formulate into forms applicable to organisms. Another problem of the bacterial cell components is low interaction with cells due to their large molecular weights and negative chargeability. Accordingly, carriers containing surfactants, lipid membrane structures, and the like have been proposed as carriers for the bacterial cell components. For example, a preparation for cancer immunotherapy comprising a bacterial cell component, an oil substance, a surfactant, and a stabilizer (Patent Literature 1) has been disclosed. In addition, the present inventors have disclosed a liposome comprising a bacterial cell component in a lipid membrane (Patent Literature 2).

CITATION LIST

Patent Literature

Patent Literature 1: International Publication No. WO2000/03724

Patent Literature 2: International Publication No. WO2007/132790

SUMMARY OF THE INVENTION

Technical Problem

From the description of Patent Literature 1, however, it is not clear whether or not the preparation for cancer immunotherapy described in Patent Literature 1 encapsulates a bacterial cell component. If the preparation is interpreted as encapsulating a bacterial cell component, its particle size as large as a size exceeding at least 2 μm makes filtration sterilization difficult. The liposome described in Patent Literature 2 has a lipid membrane comprising a bacterial cell component, i.e., comprises the bacterial cell component integrally with the lipid membrane. The liposome, however, is not a lipid membrane structure encapsulating the bacterial cell component. Although Patent Literatures 1 and 2 describe the production of an oil-in-water emulsion preparation, the production method has no step of preparing a polar solvent solution containing an empty lipid membrane structure. As a result, a lipid membrane structure having a particle size that permits filtration sterilization and encapsulating a substance of interest having dispersibility in a non-polar solvent has not yet been produced.

The present invention has been made to solve such problems, and an object of the present invention is to provide a lipid membrane structure having a particle size that permits filtration sterilization, comprising a lipid bound with a peptide consisting of a plurality of arginine residues as a constituent lipid and encapsulating a bacterial cell component having dispersibility in a non-polar solvent, and a method for producing a lipid membrane structure having a particle size that permits filtration sterilization and encapsulating a substance of interest having dispersibility in a non-polar solvent.

Solution to Problem

The present inventors have conducted diligent studies and consequently completed the present invention by finding that: a lipid membrane structure having a particle size that permits filtration sterilization and encapsulating a substance of interest having dispersibility in a non-polar solvent can be produced by mixing a polar solvent solution containing a lipid membrane structure encapsulating no substance of interest with a non-polar solvent solution in which the substance of interest dispersed to prepare an oil-in-water emulsion, and then distilling off the non-polar solvent under reduced pressure; and the thus-produced lipid membrane structure which has a particle size that permits filtration sterilization, comprises a lipid bound with a peptide consisting of a plurality of arginine residues as a constituent lipid, and encapsulates a bacterial cell component having dispersibility in a non-polar solvent can attain the treatment of bladder cancer or the inhibition of the progression thereof and activate cellular immunity.

(1) A lipid membrane structure having a particle size that permits filtration sterilization, comprising a lipid bound with a peptide consisting of a plurality of arginine residues as a constituent lipid and encapsulating a bacterial cell component having dispersibility in a non-polar solvent.

(2) The lipid membrane structure according to (1), wherein the bacterial cell component is cell-wall fraction (CW) or cell-wall skeleton fraction (CWS) of one or more bacteria selected from the group consisting of a bacterium of the genus *Mycobacterium*, a bacterium of the genus *Nocardia*, a bacterium of the genus *Corynebacterium*, and a bacterium of the genus *Rhodococcus*.

(3) The lipid membrane structure according to (2), wherein the bacterium of the genus *Mycobacterium* is *Mycobacterium Bovis bacillus* Calmette-Guerin (BCG).

(4) The lipid membrane structure according to any of (1) to (3), wherein the lipid membrane structure having a particle size that permits filtration sterilization is a lipid membrane structure having a particle size of 180 nm or smaller.

(5) A pharmaceutical composition comprising a lipid membrane structure according to any of (1) to (4).

(6) The pharmaceutical composition according to (5), wherein the pharmaceutical composition is a therapeutic agent for bladder cancer and/or an agent inhibiting the progression thereof.

(7) A method for producing a lipid membrane structure having a particle size that permits filtration sterilization and encapsulating a substance of interest having dispersibility in a non-polar solvent, comprising the following steps (i) to (iv):

(i) preparing a polar solvent solution containing a lipid membrane structure encapsulating no substance of interest;

(ii) preparing a non-polar solvent solution in which the substance of interest dispersed;

(iii) mixing the polar solvent solution containing a lipid membrane structure encapsulating no substance of interest with the non-polar solvent solution in which the substance of interest dispersed to prepare an oil-in-water emulsion; and (iv) distilling off the non-polar solvent under reduced pressure from the oil-in-water emulsion.

(8) The method according to (7), wherein the lipid membrane structure encapsulating no substance of interest is a lipid membrane structure comprising a lipid bound with a peptide consisting of a plurality of arginine residues as a constituent lipid and encapsulating no substance of interest.

(9) The method according to (7) or (8), wherein the substance of interest is a bacterial cell component.

(10) The method according to (9), wherein the bacterial cell component is cell-wall fraction (CW) or cell-wall skeleton fraction (CWS) of one or more bacteria selected from the group consisting of a bacterium of the genus *Mycobacterium*, a bacterium of the genus *Nocardia*, a bacterium of the genus *Corynebacterium*, and a bacterium of the genus *Rhodococcus*.

(11) The method according to (10), wherein the bacterium of the genus *Mycobacterium* is *Mycobacterium Bovis bacillus* Calmette-Guerin (BCG).

(12) The method according to any of (7) to (11), wherein the particle size that permits filtration sterilization is a particle size of 180 nm or smaller.

Advantageous Effects of Invention

According to the lipid membrane structure according to the present invention and the method for producing the same, a lipid membrane structure that encapsulates a bacterial cell component, can be easily formulated through dispersion in an aqueous solution, and is efficiently taken up into cells can be obtained. A lipid membrane structure encapsulating a compactly folded particle form (particle size: approximately 100 nm) of a *Mycobacterium Bovis bacillus* Calmette-Guerin cell-wall skeleton (BCG-CWS) fraction having a large conformation of approximately 1 μm in diameter in a polar solvent can be obtained. Further, a lipid membrane structure having a particle size that permits filtration sterilization can be obtained. Hence, the lipid membrane structure according to the present invention eliminates the need of sterilization in the overall production process thereof for pharmaceutical use and can thus be pharmaceutically produced inexpensively by filtration sterilization. Furthermore, the lipid membrane structure according to the present invention has a remarkably small content of a solvent and mainly encapsulates a substance of interest such as a bacterial cell component. Hence, the obtained lipid membrane structure can efficiently deliver the substance of interest. In addition, the lipid membrane structure can be efficiently taken up into cancer cells to attain the treatment of cancer or the inhibition of the progression thereof. Particularly, the lipid membrane structure can be intravesically administered to an organism to attain the treatment of bladder cancer or the inhibition of the progression thereof. Further, the lipid membrane structure can act on immunocytes to activate cellular immunity. Furthermore, the method for producing the lipid membrane structure according to the present invention can allow the lipid membrane structure to encapsulate the great majority of the substance of interest used in production so that the lipid membrane structure can efficiently encapsulate the substance of interest.

DETAILED DESCRIPTION OF THE INVENTION

Figure 1:
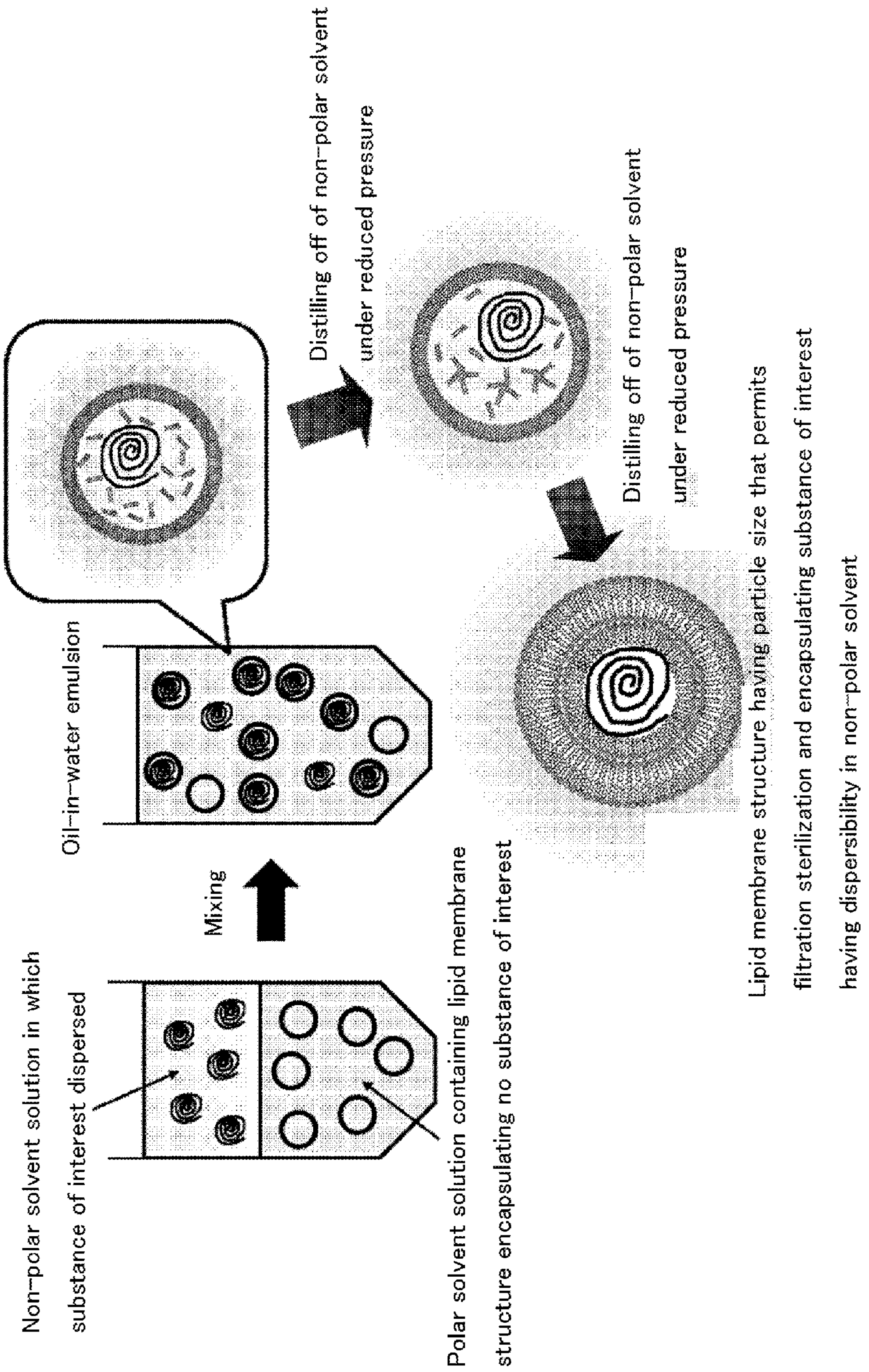
FIG. 1 is a diagram schematically showing a method for producing the lipid membrane structure according to the present invention.

Hereinafter, the lipid membrane structure encapsulating a bacterial cell component having dispersibility in a non-polar solvent according to the present invention and the method for producing the same will be described in detail. The lipid membrane structure according to the present invention has a particle size that permits filtration sterilization, comprises a lipid bound with a peptide consisting of a plurality of arginine residues as a constituent lipid, and encapsulates a bacterial cell component having dispersibility in a non-polar solvent.

The "filtration sterilization" refers to the operation of removing microbes including yeasts and bacteria by filtration. The filtration sterilization of the lipid membrane structure can be carried out, for example, through a generally commercially available membrane filter for filtration sterilization having a pore size of 0.2, 0.22, 0.45, or 5.0 μm, or the like. Examples of the "particle size that permits filtration sterilization" according to the present invention can preferably include particle sizes of 150 nm or larger and smaller than 200 nm and can more preferably include particle sizes of 155 nm or larger and 195 nm or smaller, further preferably 190, 187, 185, 183, 181, 180, 179, 178, 177, 176, 175, 174, 173, 172, 171, 170, 169, 168, 167, 166, 165, 164, 163, 162, 161, and 160 nm.

In a preferred embodiment, the lipid membrane structure according to the present invention is a closed vesicle having lipid membrane(s) composed of a lipid monolayer or a lipid bilayer. In this context, since the lipid membrane structure according to the present invention encapsulates a substance of interest such as a bacterial cell component having dispersibility in a non-polar solvent, the innermost lipid membrane may form a lipid membrane of a lipid monolayer in which lipid molecules are arranged with their hydrophobic groups facing the lumen (substance of interest).

The number of lipid membrane(s) carried by the lipid membrane structure according to the present invention may be 1 or may be 2 or more. Specific examples of the lipid membrane structure can include a multilamellar liposome vesicle (MLV) having a plurality of lipid membranes each composed of a lipid bilayer as well as unilamellar liposomes having only one lipid membrane composed of a lipid bilayer, such as a small unilamellar vesicle (SUV), a large unilamellar vesicle (LUV), and a giant unilamellar vesicle (GUV).

The lipid constituting the lipid membrane structure according to the present invention (hereinafter, this lipid is referred to as a "constituent lipid") is not limited by its type. Examples of the lipid can include phospholipids, glycolipids, sterols, long-chain aliphatic alcohols, and glycerin fatty acid esters, any of which can be used. Also, any of cationic lipids, pH-dependent cationic lipids, neutral lipids, and anionic lipids can be used.

Examples of the phospholipids can include phosphatidylcholines (e.g., dioleoylphosphatidylcholine, dilauroylphosphatidylcholine, dimyristoylphosphatidylcholine, dipalmitoylphosphatidylcholine, distearoylphosphatidylcholine, and egg-yolk phosphatidylcholine (EPC)), phosphatidylglycerols (e.g., dioleoylphosphatidylglycerol, dilauroylphosphatidylglycerol, dimyristoylphosphatidylglycerol, dipalmitoylphosphatidylglycerol, and distearoylphosphatidylglycerol), phosphatidylethanolamines (e.g., dioleoylphosphatidylethanolamine, dilauroylphosphatidylethanolamine, dimyristoylphosphatidylethanolamine, dipalmitoylphosphatidylethanolamine, distearoylphosphatidylethanolamine (DSPE), and dioleoylglycerophosphoethanolamine (DOPE)), phosphatidylserine, phosphatidylinositol, phosphatidic acid, cardiolipin, and their hydrogenation products, and natural lipids derived from egg yolk, soybean, or other animals or plants (e.g., egg-yolk lecithin and soybean lecithin). One or more of these phospholipids can be used.

Examples of the glycolipids can include: sphingomyelins; glyceroglycolipids such as sulfoxyribosyl glyceride, diglycosyl diglyceride, digalactosyl diglyceride, galactosyl diglyceride, and glycosyl diglyceride; and sphingoglycolipids such as galactosyl cerebroside, lactosyl cerebroside, and ganglioside. One or more of these glycolipids can be used.

Examples of the sterols can include: animal-derived sterols such as cholesterol (Chol), cholesterol succinate, lanosterol, dihydrolanosterol, desmosterol, and dihydrocholesterol; plant-derived sterols (phytosterols) such as stigmasterol, sitosterol, campesterol, and brassicasterol; and microbe-derived sterols such as zymosterol and ergosterol. One or more of these sterols can be used. These sterols can generally be used for physically or chemically stabilizing lipid bilayers or for adjusting membrane fluidity.

A fatty acid having 10 to 20 carbon atoms or an alcohol thereof can be used as a long-chain fatty acid or a long-chain aliphatic alcohol. Examples of such long-chain fatty acids or long-chain aliphatic alcohols can include: saturated fatty acids such as palmitic acid, stearic acid (STR), lauric acid, myristic acid, pentadecylic acid, arachidic acid, margaric acid, and tuberculostearic acid; unsaturated fatty acids such as palmitoleic acid, oleic acid, arachidonic acid, vaccenic acid, linoleic acid, linolenic acid, arachidonic acid and eleostearic acid; and oleyl alcohol, stearyl alcohol, lauryl alcohol, myristyl alcohol, cetyl alcohol, and linoleyl alcohol. Specific examples thereof can include 1,2-dimyristoyl-sn-glycerol (DMG) and 1,2-distearoyl-sn-glycerol (DSG). One or more of these long-chain fatty acids or long-chain aliphatic alcohols can be used.

Examples of the glycerin fatty acid esters can include monoacyl glyceride, diacyl glyceride, and triacyl glyceride. One or more of these glycerin fatty acid esters can be used.

Examples of the cationic lipids can include the lipids mentioned above as well as diethanolamine hydrochloride such as diethanolamine chloride (DC-6-14), cholesteryl hexadecyl ether (CHE), dioctadecyldimethylammonium chloride (DODAC), N-(2,3-dioleyloxy)propyl-N,N,N-trimethylammonium (DOTMA), didodecylammonium bromide (DDAB), 1,2-dioleoyloxy-3-trimethylammonio propane (DOTAP), 3β-N—(N',N',-dimethyl-aminoethane)-carbamol cholesterol (DC-Chol), 1,2-dimyristoyloxypropyl-3-dimethylhydroxyethyl ammonium (DMRIE), and 2,3-dioleyloxy-N-[2(sperminecarboxamido)ethyl]-N,N-dimethyl-1-propanaminum trifluoroacetate (DOSPA). One or more of these cationic lipids can be used.

Examples of the pH-dependent cationic lipids can include 1-methyl-4,4-bis[(9Z,12Z)-octadeca-9,12-dien-1-yloxy]piperidine (YSK05) and 1,2-dioleoyl-3-dimethylammonium propane (DODAP). One or more of these pH-dependent cationic lipids can be used.

Examples of the neutral lipids can include the lipids mentioned above as well as diacylphosphatidylcholine, diacylphosphatidylethanolamine, ceramide, and dimyristoylglycerol (Cl4). One or more of these neutral lipids can be used. Examples of the anionic lipids can include the lipids mentioned above as well as diacylphosphatidylserine, diacylphosphatidic acid, and N-succinylphosphatidylethanolamine (N-succinyl PE), phosphatidyl ethylene glycol. One or more of these anionic lipids can be used.

The number of arginine residues in the peptide consisting of a plurality of arginine residues according to the present invention (hereinafter, referred to as a "peptide according to the present invention") is not particularly limited as long as it is two or more. Examples of the number of arginine residues can include several, a dozen, and several dozens and can more specifically include 2 to 20, preferably 3 to 18, more preferably 4 to 16, further preferably 5, 6, 7, 8, 9, 10, 11, 12, 13, 14, and 15. The peptide according to the present invention can be synthesized using a method appropriately selectable by those skilled in the art on the basis of the sequence thereof. Examples of such methods can include: a peptide synthesis method which involves chemically polymerizing amino acids one by one to synthesize a polypeptide; a method which involves preparing recombinant vectors containing DNA encoding the peptide according to the present invention, transferring the prepared vectors into appropriate host cells, and culturing the resulting transformants in a medium, followed by collection from the obtained cultures; and a method which involves expressing DNA encoding the peptide according to the present invention in a cell-free protein synthesis system. General methods widely known to those skilled in the art or any of other methods can be used in these synthesis methods.

The "lipid bound with a peptide consisting of a plurality of arginine residues" according to the present invention may be a lipid bound with the N terminus of the peptide according to the present invention or may be a lipid bound with the C terminus of the peptide according to the present invention. In the present invention, the peptide according to the present invention and the lipid may be connected directly or may be connected via some linker such as an amino acid (e.g., proline, isoleucine, leucine, or valine), a peptide (e.g., polyproline), or a hydrophilic polymer (e.g., polyethylene glycol (PEG)).

Examples of the binding pattern between the peptide according to the present invention and the lipid can include: noncovalent bonds such as hydrogen bonds, ionic bonds, hydrophobic bonds, and van der Waals bonds; and covalent bonds such as disulfide bonds and peptide bonds. Examples of the lipid in the "lipid bound with a peptide consisting of a plurality of arginine residues" can include those listed above for use as the constituent lipid of the lipid membrane structure according to the present invention. In Examples mentioned later, stearic acid bound with a peptide (SEQ ID NO: 1) consisting of 8 arginine residues (stearylated octaarginine: STR-R8) was used as a "peptide-bound lipid".

The lipid membrane of the lipid membrane structure according to the present invention may comprise plural types of "lipids each bound with a peptide consisting of a plurality of arginine residues". For example, STR-R8 and palmitic acid bound with a peptide consisting of 8 arginine residues, phospholipid bound with a peptide consisting of 10 arginine residues and sterol bound with a peptide consisting of 7 arginine residues, or stearic acid bound with a peptide consisting of 10 arginine residues and glycolipid bound with a peptide consisting of 8 arginine residues can be arbitrarily selected. Also, the content of the "lipid bound with a peptide consisting of a plurality of arginine residues" can be appropriately determined according to the number of arginine residues, the type of the peptide-bound lipid, the types of other constituent lipids, the type of the bacterial cell component, etc.

The lipid membrane of the lipid membrane structure according to the present invention may contain an antioxidant such as tocopherol, propyl gallate, ascorbyl palmitate, or butylated hydroxytoluene, a charged substance that confers positive charge, such as stearylamine or oleylamine, a charged substance that confers negative charge, such as dicetyl phosphate, a membrane protein such as membrane extrinsic protein or membrane intrinsic protein, and the like, in addition to the constituent lipid. The content thereof can be appropriately adjusted.

The "non-polar solvent" refers to a solvent having no polarity or a solvent having relatively small polarity. The non-polar solvent according to the present invention is preferably a non-polar solvent having a lower boiling point than that of a polar solvent such as water, more preferably a non-polar solvent in which the bacterial cell component can be dispersed to form relatively small particles. Specific examples of the non-polar solvent according to the present invention can include pentane, diethyl ether, diisopropyl ether (isopropyl ether), hexane, tetrachloromethane, toluene, benzene, dichloromethane, chloroform, cyclohexane, and butyl acetate, and mixtures thereof with acetic acid ester, acetone, or methanol. One or more of these non-polar solvents can be used. Pentane, diethyl ether, or diisopropyl ether is preferred.

The "bacterial cell component" according to the present invention is not particularly limited as long as the bacterial cell component has dispersibility in a non-polar solvent. In this context, the phrase "having dispersibility in a non-polar solvent" according to the present invention refers to being dispersible relatively uniformly in the non-polar solvent. Examples of the bacterial cell component according to the present invention can include cell-wall fraction (CW) or cell-wall skeleton fraction (CWS) of bacteria such as a bacterium of the genus *Mycobacterium*, a bacterium of the genus *Nocardia*, a bacterium of the genus *Corynebacterium*, and a bacterium of the genus *Rhodococcus*.

The cell wall (CW) of the bacterium of the genus *Mycobacterium* contains macromolecules consisting of my colic acid (fatty acid), arabinogalactan (polysaccharide), and peptidoglycan, and these macromolecules constitute the basic structure of the cell wall. This basic structure is called a "cell wall skeleton (CWS)". A bacterium of the genus *Nocardia*, a bacterium of the genus *Corynebacterium*, a bacterium of the genus *Rhodococcus*, and the like, which are taxonomically related to the bacterium of the genus *Mycobacterium*, also have a cell wall skeleton (CWS) similar to that of the bacterium of the genus *Mycobacterium*.

Examples of the bacterium of the genus *Mycobacterium* can include tuberculosis complexes such as *M. tuberculosis, M. bovis, M. africanum, M. microti, M. canettii*, and *M. bovis* BCG. Examples of the bacterium of the genus *Nocardia* can include *N. asteroides, N. brasiliensis*, and *N. rubra*. Examples of the bacterium of the genus *Corynebacterium* can include *C. diphtheriae* and *C. ulcerans*. The "bacterial cell component" according to the present invention is preferably a cell-wall fraction (BCG-CW) or cell-wall skeleton fraction (BCG-CWS) of BCG among these bacteria.

The cell-wall fraction (CW) is not particularly limited by its composition, preparation method, etc., as long as the cell-wall fraction (CW) is composed mainly of a cell wall skeleton (CWS). The cell-wall fraction (CW) can be prepared, for example, by a method described in Patent Literature 2 mentioned above. The cell-wall skeleton fraction (CWS) refers to a fraction obtained by the purification of the cell wall skeleton (CWS) from the cell-wall fraction (CW). The cell-wall skeleton fraction (CWS) fraction can also be prepared by a method described in Patent Literature 2 mentioned above.

The cell-wall fraction (CW) or cell-well skeleton fraction (CWS) of the bacteria such as a bacterium of the genus *Mycobacterium*, a bacterium of the genus *Nocardia*, a bacterium of the genus *Corynebacterium*, and a bacterium of the genus *Rhodococcus* have anticancer effect or immunostimulatory activity (adjuvant activity or immunologically activating effect). In the cell wall skeleton (CWS), the peptidoglycan moiety and the mycolic acid moiety are important for the anticancer effect or the immunostimulatory activity. Components (e.g., lipomannan and trehalose mycolate) other than the cell wall skeleton (CWS) contained in the cell-wall fraction (CW) also contribute to the anticancer effect or the immunostimulatory activity.

The present invention also provides a pharmaceutical composition comprising the lipid membrane structure according to the present invention. The description about a constitution equivalent to or corresponding to the aforementioned lipid membrane structure encapsulating a bacterial cell component having dispersibility in a non-polar solvent will be omitted as to the pharmaceutical composition comprising the lipid membrane structure according to the present invention. The pharmaceutical composition comprising the lipid membrane structure according to the present invention can be used in pharmaceutical application according to the effects of the bacterial cell component. When the bacterial cell component has, for example, anticancer effect or immunostimulatory activity, the pharmaceutical composition comprising the lipid membrane structure of the present invention can be used as a therapeutic agent for cancers such as bladder cancer, pharyngeal cancer, stomach cancer, lung cancer, skin cancer, liver cancer, pancreas cancer, colon cancer, uterine cancer, and prostate cancer or an agent inhibiting the progression thereof, or as an immunostimulator (adjuvant).

Examples of the dosage form of the pharmaceutical composition can include dispersions of the lipid membrane structure and dried products (e.g., freeze-dried products and spray-dried products) thereof. For example, saline or a buffer solution such as a phosphate buffer solution, a citrate buffer solution, or an acetate buffer solution can be used as the dispersion solvent. The dispersion may be supplemented with additives, for example, saccharides, polyhydric alcohols, water-soluble polymers, nonionic surfactants, antioxidants, pH adjusters, and hydration promoters, and used.

The pharmaceutical composition can be used both in vivo and in vitro. In the case of using the pharmaceutical composition in vivo, examples of its administration routes can include oral administration as well as parenteral administration such as intravesical administration, intravenous administration, intraperitoneal administration, subcutaneous administration, and transnasal administration. The dose and the frequency of administration thereof can be appropriately determined according to the age, sex, and symptoms of a recipient, the type and amount of the bacterial cell component, etc.

The present invention further provides a method for producing the lipid membrane structure encapsulating a substance of interest having dispersibility in a non-polar solvent. The method for producing the lipid membrane structure according to the present invention is schematically shown in FIG. 1. The method for producing the lipid membrane structure according to the present invention is a method for producing a lipid membrane structure having a particle size that permits filtration sterilization and encapsulating a substance of interest having dispersibility in a non-polar solvent, comprising the following steps (i) to (iv):

(i) preparing a polar solvent solution containing a lipid membrane structure encapsulating no substance of interest;

(ii) preparing a non-polar solvent solution in which the substance of interest dispersed;

(iii) mixing the polar solvent solution containing a lipid membrane structure encapsulating no substance of interest with the non-polar solvent solution in which the substance of interest dispersed to prepare an oil-in-water emulsion; and (iv) distilling off the non-polar solvent under reduced pressure from the oil-in-water emulsion.

The description about a constitution equivalent to or corresponding to the aforementioned lipid membrane structure encapsulating a bacterial cell component having dispersibility in a non-polar solvent or the aforementioned pharmaceutical composition comprising the lipid membrane structure according to the present invention will be omitted as to the method for producing the lipid membrane structure encapsulating a substance of interest having dispersibility in a non-polar solvent according to the present invention.

The "substance of interest" according to the present invention is not particularly limited as long as the substance of interest has dispersibility in a non-polar solvent. Examples of the "substance of interest" according to the present invention can include various biologically active substances such as drugs, nucleic acids, peptides, proteins, sugars, and complexes thereof. A bacterial cell component is preferred.

The step (i) of preparing a polar solvent solution containing a lipid membrane structure encapsulating no substance of interest may be performed by a non-limiting method and can be carried out according to a routine method. Examples of such methods can include methods which involve preparing the lipid membrane structure encapsulating no substance of interest by a method known in the art, such as a hydration method, a sonication method, an ethanol injection method, an ether injection method, a reverse-phase evaporation method, a surfactant method, or a freezing-thawing method, using a polar solvent. Alternatively, the lipid membrane structure may be prepared according to a routine method, then recovered, and added to a desired polar solvent to prepare a polar solvent solution, or the external solution of the lipid membrane structure may be replaced with a desired polar solvent by dialysis or the like to prepare a polar solvent solution. The number of lipid membrane(s) in the "lipid membrane structure encapsulating no substance of interest" may be 1 or may be 2 or more. Examples of the constituent lipid of the "lipid membrane structure encapsulating no substance of interest" can include the lipids listed above.

In this context, the "polar solvent" refers to a solvent having relatively large polarity. The polar solvent according to the present invention is preferably a polar solvent having a higher boiling point than that of a non-polar solvent constituting an oil-in-water emulsion in the step (iii), because the non-polar solvent can be easily distilled off under reduced pressure. Specific examples of the polar solvent according to the present invention can include water, ethanol, acetic acid, acetonitrile, and acetone. One or more of these polar solvents can be used.

Examples of the method for preparing a non-polar solvent solution in which the substance of interest dispersed in the step (ii) can include methods which involve adding the substance of interest to a non-polar solvent, followed by stirring. In this context, the non-polar solvent is preferably a non-polar solvent that can be distilled off under reduced pressure from an oil-in-water emulsion in the step (iii), i.e., a non-polar solvent having a lower boiling point than that of the polar solvent constituting the oil-in-water emulsion. Specific examples thereof can include those listed above as the "non-polar solvent" for the lipid membrane structure according to the present invention.

The step (iii) of mixing the polar solvent solution containing a lipid membrane structure encapsulating no substance of interest with the non-polar solvent solution in which the substance of interest dispersed to prepare an oil-in-water emulsion can be carried out according to a routine method. Examples of such methods can include a method which involves stirring the mixture using a vortex mixer and a method which involves sonicating the mixture using a sonicator. These methods can be appropriately selected according to the types and amounts of the polar solvent and the non-polar solvent.

Examples of the method for distilling off the non-polar solvent under reduced pressure from the oil-in-water emulsion in the step (iv) can include methods which involve applying the oil-in-water emulsion to an evaporator. In this case, the water bath temperature and rotational speed of the evaporator, the duration for which the oil-in-water emulsion is applied to the evaporator, and the like can be appropriately determined according to the types and amounts of the polar solvent and the non-polar solvent, etc.

The lipid membrane structure according to the present invention and the lipid membrane structure produced by the method for producing the lipid membrane structure according to the present invention can be dispersed, for use, in an appropriate aqueous solvent such as saline, a phosphate buffer solution, a citrate buffer solution, or an acetate buffer solution. The dispersion may be appropriately supplemented with additives, for example, saccharides, polyhydric alcohols, water-soluble polymers, nonionic surfactants, antioxidants, pH adjusters, and hydration promoters. The lipid membrane structure can be stored in a dried state of the dispersion. In addition, the lipid membrane structure can be orally administered and may also be parenterally administered, for example, through an intravesical, intravenous, intraperitoneal, subcutaneous, or transnasal route.

Hereinafter, the lipid membrane structure encapsulating a bacterial cell component having dispersibility in a non-polar solvent according to the present invention and the method for producing the same will be described with reference to Examples. It should be understood that the technical scope of the present invention is not limited by features shown by these Examples.

EXAMPLES

<Example 1> Preparation of Liposome (1) Liposome Encapsulating BCG-CWS

[1-1] Preparation of HBS Containing Empty Liposome

Stearic acid (STR-R8; Kurabo Industries Ltd.) bound with a peptide (SEQ ID NO: 1; hereinafter, referred to as "R8") consisting of arginine residues was prepared. The peptide R8 is known to impart a given internalization ability to liposomes (International Publication No. WO2005/032593; and Kentaro Kogure, Yakugaku Zasshi (Journal of the Pharmaceutical Society of Japan), Vol. 127, No. 10, p. 1685-1691, 2007). STR-R8 has a structure in which stearic acid (STR) is bound with the N terminus of R8. Subsequently, a liposome was prepared by the hydration method using egg-yolk phosphatidylcholine (EPC), cholesterol (Chol), and STR-R8. Specifically, these lipids were dissolved at a molar ratio of EPC:Chol:STR-R8=70:30:2 in chloroform. This solution was used as a lipid chloroform solution (total lipid concentration: 10 mmol/L). The lipid chloroform solution was placed in an eggplant-shaped flask and dried under reduced pressure using an evaporator to obtain a lipid film. The lipid film was hydrated by the addition of 5 mmol/L HEPES-buffered saline (5 mmol/L HEPES and 0.9 w/v % NaCl; hereinafter, referred to as "HBS") having a pH of 7.4, and stirred or sonicated to prepare a liposome, which was used as an empty liposome. The empty liposome encapsulated no substance of interest and had a lumen filled with HBS. Subsequently, the empty liposome was filtered through a polycarbonate membrane filter (Nucleopore Corp.) having a pore size of 400 nm using Mini Extruder (Avanti Polar Lipids, Inc.) to prepare HBS containing an empty liposome having a pore size of 400 nm or smaller.

[1-2] Preparation of Solution Containing BCG-CWS Dispersed in Non-Polar Solvent

Figure 2:
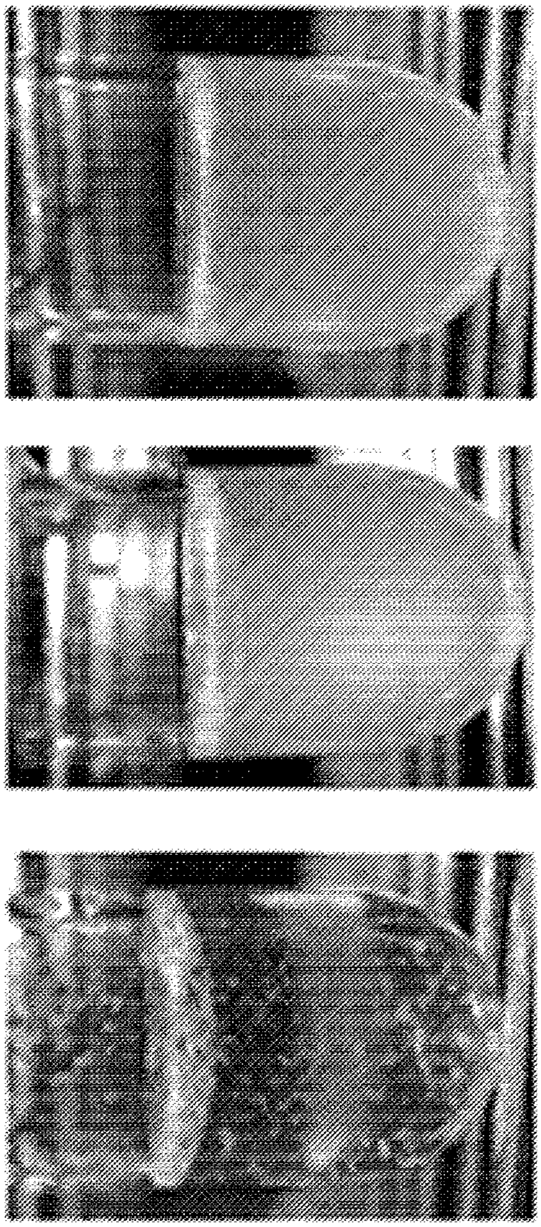
FIG. 2 is a diagram showing the appearances of HBS, ethanol, and pentane containing BCG-CWS.

A *Mycobacterium Bovis bacillus* Calmette-Guerin cell-wall skeleton (BCG-CWS) fraction was obtained according to the method described in the previous report (Patent Literature 2). Subsequently, for a preliminary experiment, 1 mg of BCG-CWS was added to 300 μL each of HBS, ethanol, and pentane and stirred to confirm their appearances. The results are shown in FIG. 2. As shown in FIG. 2, BCG-CWS aggregated in HBS to form a visibly large particle. By contrast, BCG-CWS was dispersed in ethanol and pentane without aggregating. This demonstrated that BCG-CWS is dispersed in an organic solvent without aggregating.

Accordingly, next, 1 mg of BCG-CWS was added to 300 μL each of polar solvents and non-polar solvents and dispersed by stirring. The particle size and phase Doppler interferometer (PDI) of BCG-CWS in these solvents were measured using ZETASIZER Nano ZEN3600 (Malvern Instruments Ltd.). The polar solvents used were ethanol, 2-propanol, and tert-butyl alcohol, and the non-polar solvents used were pentane, diethyl ether, diisopropyl ether, and hexane. The results are shown in Table 1. As shown in Table 1, both of the particle size and PDI were remarkably small values for pentane, diethyl ether, diisopropyl ether, and hexane as compared with ethanol, 2-propanol, and tert-butyl alcohol. This demonstrated that BCG-CWS in a non-polar solvent has a smaller particle size and also a smaller variation in particle size than those of BCG-CWS in a polar solvent. These results showed that a bacterial cell component dispersed in a non-polar solvent has a small particle size and has a relatively uniform particle size. Thus, 1 mg of BCG-CWS was added to 300 μL each of pentane, diethyl ether, diisopropyl ether, and hexane and dispersed, and these dispersions were each used as a non-polar solvent solution of BCG in the subsequent experiments.

TABLE 1

| | Solvent | Particle size (nm) | PDI |
|---|---|---|---|
| Polar solvent | Ethanol | 2276 ± 1702 | 0.516 ± 0.375 |
| | 2-Propanol | 2222 ± 636 | 0.438 ± 0.322 |
| | tert-Butyl alcohol | 3235 ± 841 | 0.359 ± 0.367 |
| Non-Polar solvent | Pentane | 96 ± 1 | 0.106 ± 0.041 |
| | Diethyl ether | 104.8 | 0.212 |
| | Diisopropyl ether | 121 ± 3 | 0.291 ± 0.225 |
| | Hexane | 130 ± 5 | 0.141 ± 0.034 |

Figure 3:
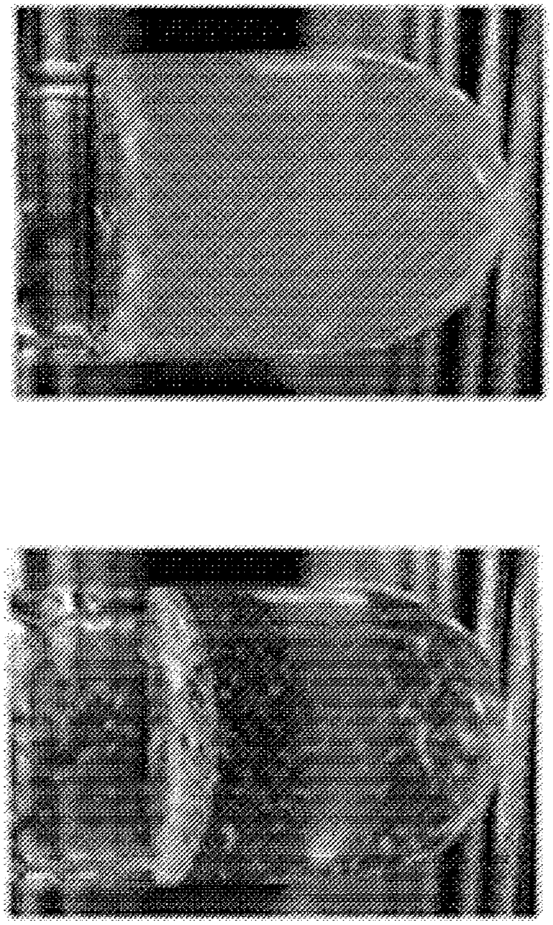
FIG. 3 is a diagram showing the appearances of HBS containing BCG-CWS and HBS containing a liposome encapsulating BCG-CWS.
Figure 4:
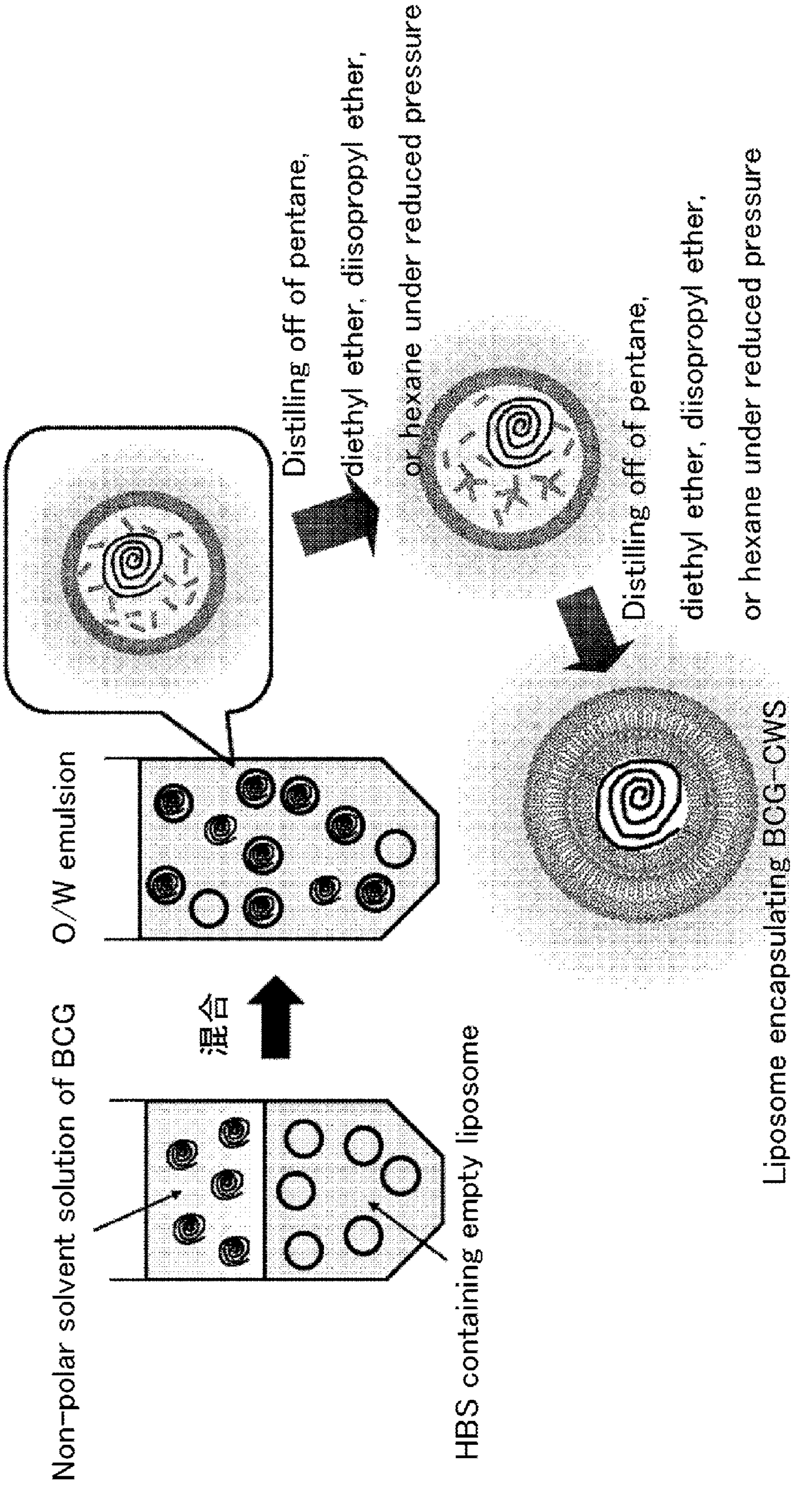
FIG. 4 is a schematic diagram showing one embodiment of a method for preparing a liposome encapsulating BCG-CWS.

[1-3] Preparation of Oil-in-Water Emulsion and Distilling Off of Non-Polar Solvent Under Reduced Pressure The HBS containing an empty liposome of Example 1(1)[1-1] was added in an amount of 700 μL to 300 μL of each non-polar solvent solution of BCG of Example 1(1) [1-2] and mixed therewith by sonication using a probe-type sonicator to prepare an oil-in-water emulsion (O/W emulsion). Subsequently, the O/W emulsion was transferred to an eggplant-shaped flask and subjected to evaporation using an evaporator so that pentane, diethyl ether, diisopropyl ether, or hexane was distilled off under reduced pressure to prepare a liposome, which was used as a liposome encapsulating BCG-CWS. Subsequently, each liposome encapsulating BCG-CWS was filtered through a polycarbonate membrane filter (Nucleopore Corp.) having a pore size of 200 nm using Mini Extruder (Avanti Polar Lipids, Inc.). The appearance of HBS containing the liposome encapsulating BCG-CWS was compared with the appearance of HBS containing BCG-CWS. The results are shown in FIG. 3. As mentioned above, BCG-CWS aggregated in HBS to form a visibly large particle, whereas the liposome encapsulating BCG-CWS was confirmed to be dispersed in HBS as shown in FIG. 3. The method for preparing the liposome encapsulating BCG-CWS according to Examples 1(1)[1-1] to 1(1)[1-3] is schematically shown in FIG. 4.

(2) Liposome for Comparison

A liposome was prepared according to the methods described in Examples 1(1)[1-1] to 1(1)([1-3] and used as a liposome for comparison. However, pentane containing EPC, Chol, and STR-R8 at a molar ratio of EPC:Chol:STR-R8=70:30:2 and at a total lipid concentration of 23.3 mmol/L and containing BCG-CWS at a concentration of 1 mg/300 μL was used instead of the non-polar solvent solution of BCG, and HBS was used instead of the HBS containing an empty liposome.

(3) Liposomes Containing Varying Amounts of R8

Liposomes were prepared according to the method described in Example 1(1)[1-1] except that the ratio of the lipids in the lipid chloroform solution was changed to EPC:Chol:STR-R8=70:30:0, 1, 2, 3, 4, and 5 instead of EPC:Chol:STR-R8=70:30:2. Specifically, empty liposomes having 0, 1, 2, 3, 4, or 5% content of the R8-bound lipid as a constituent lipid with respect to the total amount of other constituent lipids were prepared and used as R8/0 to 5% empty liposomes. Next, liposomes were prepared according to the methods described in Examples 1(1)[1-2] and 1(1)[1-3] except that pentane was used as a non-polar solvent and the R8/0 to 5% empty liposomes were each used instead of the empty liposome. These liposomes were used as R8/0 to 5% liposomes.

(4) Liposome Containing BCG-CWS in Lipid Membrane

Figure 5:
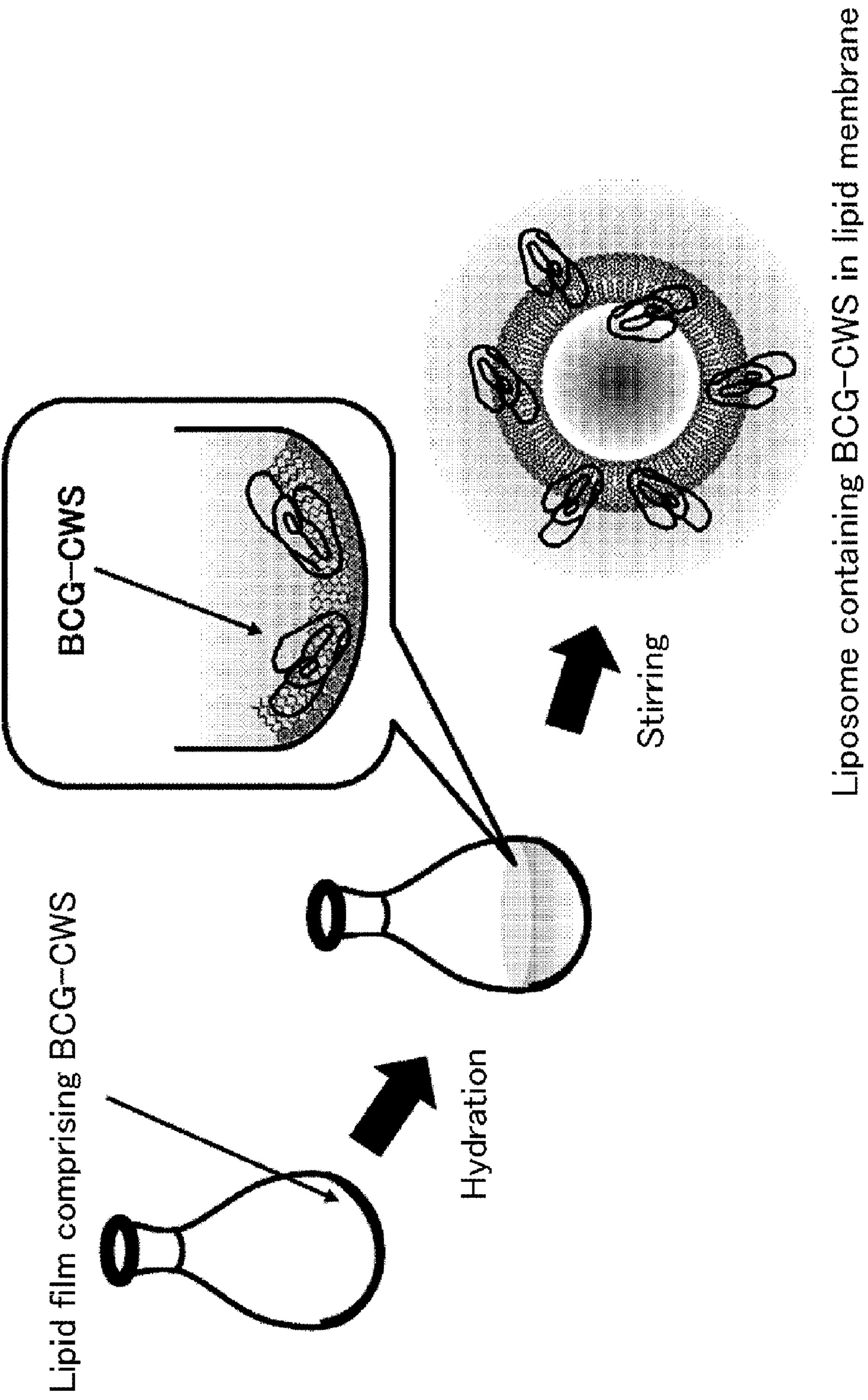
FIG. 5 is a schematic diagram showing a method for preparing a liposome containing BCG-CWS in a lipid membrane (conventional form).

A liposome having a lipid membrane comprising BCG-CWS was prepared according to the method described in the previous report (International Publication No. WO2007/132790) and used as a liposome containing BCG-CWS in a lipid membrane. Specifically, EPC and Chol were first dissolved at a molar ratio of EPC:Chol=7:3 in chloroform to obtain an EPC/Chol solution (total lipid concentration: 10 mmol/L). Also, STR-R8 was dissolved at a concentration of 10 mmol/L in water to obtain an aqueous STR-R8 solution. Further, 1 mg of BCG-CWS was suspended in a chloroform/ethanol mixed solvent of chloroform:ethanol=2:1 (v:v) to obtain a BCG-CWS suspension. Subsequently, the whole amount of the BCG-CWS suspension (amount of BCG-CWS: 1 mg) was mixed with the EPC/Chol solution and the aqueous STR-R8 solution at a ratio of 100:2 (v:v) to obtain a mixed lipid solution of BCG. The mixed lipid solution of BCG was applied to an evaporator and dried under reduced pressure to prepare a lipid film. The lipid film was hydrated by the addition of 700 μL of HBS. Then, glass beads were added thereto and stirred by the rotation of a rotary evaporator at 65° C. for 20 minutes without reduction in pressure to prepare a liposome containing BCG-CWS in a lipid membrane. Subsequently, the liposome was filtered through membrane filters having pore sizes of 1,000 nm and 400 nm. The method for preparing the liposome containing BCG-CWS in a lipid membrane according to Example 1(4) is schematically shown in FIG. 5.

<Example 2> Properties of Liposome (1) Particle Size, PDI, Zeta Potential, and Rate of Encapsulation or Content of BCG-CWS

[1-1] Measurement Method

The particle size, PDI, and zeta potential of each liposome were measured by the dynamic light scattering method for the particle size and PDI and by electrophoresis for the zeta potential using ZETASIZER Nano ZEN3600 (Malvern Instruments Ltd.).

The rate of encapsulation or content of BCG-CWS of each liposome was also measured as follows: first, BCG-CWS was suspended at a concentration of 0.05 mg/mL, 0.25 mg/mL, or 0.1 mg/mL in ethanol, and these suspensions were each used as a sample for calibration. Also, HBS containing each liposome was used as a sample for assay. Water and phenol were added to a 1.1% (v/v) fuchsin solution (Nacalai Tesque, Inc.) to adjust the final concentration of phenol to 5% (w/v) and the final concentration of fuchsin to 0.55% (v/v). This solution was used as a fuchsin/phenol solution. Next, 1 mL of 100% ethanol was placed in each microtube. Further, 1 mL of 100% ethanol (negative control), 1 mL of each sample for calibration, or 100 to 150 μL each sample for assay was placed therein. These microtubes were vortexed for 2 minutes to deposit BCG-CWS. The pellet of the deposited BCG-CWS was visually confirmed and then centrifuged for 5 minutes under conditions of 15° C. and 6000 rpm to remove the supernatant and recover the pellet. Subsequently, 1 mL of 100% ethanol was added thereto, and centrifugation was performed under the same conditions as above to remove the supernatant and recover the pellet. The pellet was dried in air for 10 minutes. Then, 400 μL of hexane was added thereto, and BCG-CWS was dispersed into hexane by vortex or sonication. Subsequently, 200 μL of the fuchsin/phenol solution was added to the dispersion and inverted for 3 to 4 minutes to stain BCG-CWS with fuchsin. In this context, mycolic acid, which is a main component of BCG-CWS, is known to react with fuchsin to develop red color. Subsequently, 250 μL of the upper hexane layer was recovered and transferred to a 96-well plate, and the absorbance was measured at 530 nm. A calibration curve of BCG-CWS concentrations was prepared on the basis of the measurement results of the negative control and the samples for calibration. The measurement results of the sample for assay were fit into the prepared calibration curve to determine the BCG-CWS concentration of the sample for assay. The amount of BCG-CWS in the total amount of the liposome was calculated from this BCG-CWS concentration, and the rate of encapsulation or content of BCG-CWS was determined according to the following expression 1:

Rate of encapsulation or content of BCG-CWS (%)=100×(Amount of BCG-CWS in the total amount of the liposome/Amount of BCG-CWS used in the preparation of the liposome). Expression 1;

Specifically, the rate of encapsulation or content of BCG-CWS refers to a value indicating the ratio of BCG-CWS actually encapsulated in the liposome or contained in the lipid membrane to BCG-CWS used in the preparation of the liposome.

[1-2] Comparison Between Liposome Encapsulating BCG-CWS and Liposome Containing BCG-CWS in Lipid Membrane The particle size, PDI, zeta potential, and the rate of encapsulation or content of BCG-CWS were measured by the methods described in Example 2(1)[1-1] as to the liposomes encapsulating BCG-CWS of Example 1(1) and the liposome containing BCG-CWS in a lipid membrane of Example 1(4). The results are shown in Table 2. As shown in Table 2, PDI and the zeta potential were equivalent between each liposome encapsulating BCG-CWS and the liposome containing BCG-CWS in a lipid membrane. By contrast, the particle size was remarkably small in the liposome encapsulating BCG-CWS as compared with the liposome containing BCG-CWS in a lipid membrane. Also, the liposome encapsulating BCG-CWS has a particle size of 180 nm or smaller when prepared using any of pentane, diethyl ether, diisopropyl ether, and hexane. These results showed that the lipid membrane structure prepared by the methods shown in Examples 1(1)[1-1] to 1(1)[1-3] has a particle size that permits filtration sterilization. The rate of encapsulation or content of BCG-CWS was remarkably large in the liposome encapsulating BCG-CWS prepared using pentane or diisopropyl ether as compared with the liposome containing BCG-CWS in a lipid membrane. These results revealed that the methods shown in Examples 1(1)[1-1] to 1(1)[1-3] can allow the lipid membrane structure to efficiently encapsulate the substance of interest.

TABLE 2

| | Particle size (nm) | PDI | Zeta potential (mV) | Rate of encapsulation or content of BCG-CWS |
|---|---|---|---|---|
| Liposome encapsulation BCG-CWS (prepared using pentane) | 166 ± 4 | 0.257 ± 0.04 | 31.2 ± 0.8 | 57.0 ± 4.0 |
| Liposome encapsulation BCG-CWS (prepared using diethyl ether) | 168.1 | 0.356 | | |
| Liposome encapsulation BCG-CWS (prepared using diisopropyl ether) | 172.8 ± 5.4 | 0.293 ± 0.020 | 35.2 ± 1.0 | 50.5 ± 2.2 |
| Liposome encapsulation BCG-CWS (prepared using hexane) | 146.7 ± 5.5 | 0.199 ± 0.012 | 40.7 ± 53.2 | |
| Liposome containing BCG-CWS in lipid membrane | 496 ± 1.32 | 0.453 ± 0.08 | 33.5 ± 6.0 | 37.5 ± 8.8 |

In Examples 2(1)[1-3] and 2(2) to 2(5) and Examples 3 to 5 given below, the liposome encapsulating BCG-CWS of Example 1(1)[1-3] prepared using pentane was used.

[1-3] Comparison Between Liposome Encapsulating BCG-CWS and Liposome for Comparison The particle size, PDI, zeta potential, and the rate of encapsulation or content of BCG-CWS were measured by the methods described in Example 2(1)[1-1] as to the liposome for comparison of Example 1(2). The results are shown in Table 3 in comparison to the results about the liposome encapsulating BCG-CWS of Example 1(1). As shown in Table 3, the particle size, PDI, and the zeta potential were equivalent between the liposome encapsulating BCG-CWS and the liposome for comparison. On the other hand, the rate of encapsulation or content of BCG-CWS was remarkably large in the liposome encapsulating BCG-CWS as compared with the liposome for comparison. This revealed that for the efficient encapsulation of BCG-CWS in the liposome, it is required to mix the HBS containing an empty liposome with the non-polar solvent solution of BCG. These results showed that for the efficient encapsulation of the substance of interest in the lipid membrane structure, it is required to mix the polar solvent solution containing a lipid membrane structure encapsulating no substance of interest with the non-polar solvent solution in which the substance of interest dispersed to prepare an oil-in-water emulsion.

TABLE 3

| | Particle size (nm) | PDI | Zeta potential (mV) | Rate of encapsulation or content of BCG-CWS |
|---|---|---|---|---|
| Liposome encapsulating BCG-CWS (prepared using pentane) | 166 ± 4 | 0.257 ± 0.04 | 31.2 ± 0.8 | 57.0 ± 4.0 |
| Liposome for comparison | 157 ± 18 | 0.210 ± 0.011 | 40.0 ± 3.8 | 12 ± 19 |

[1-4] Comparison Among Liposomes Containing Varying Amounts of R8

Figure 6:
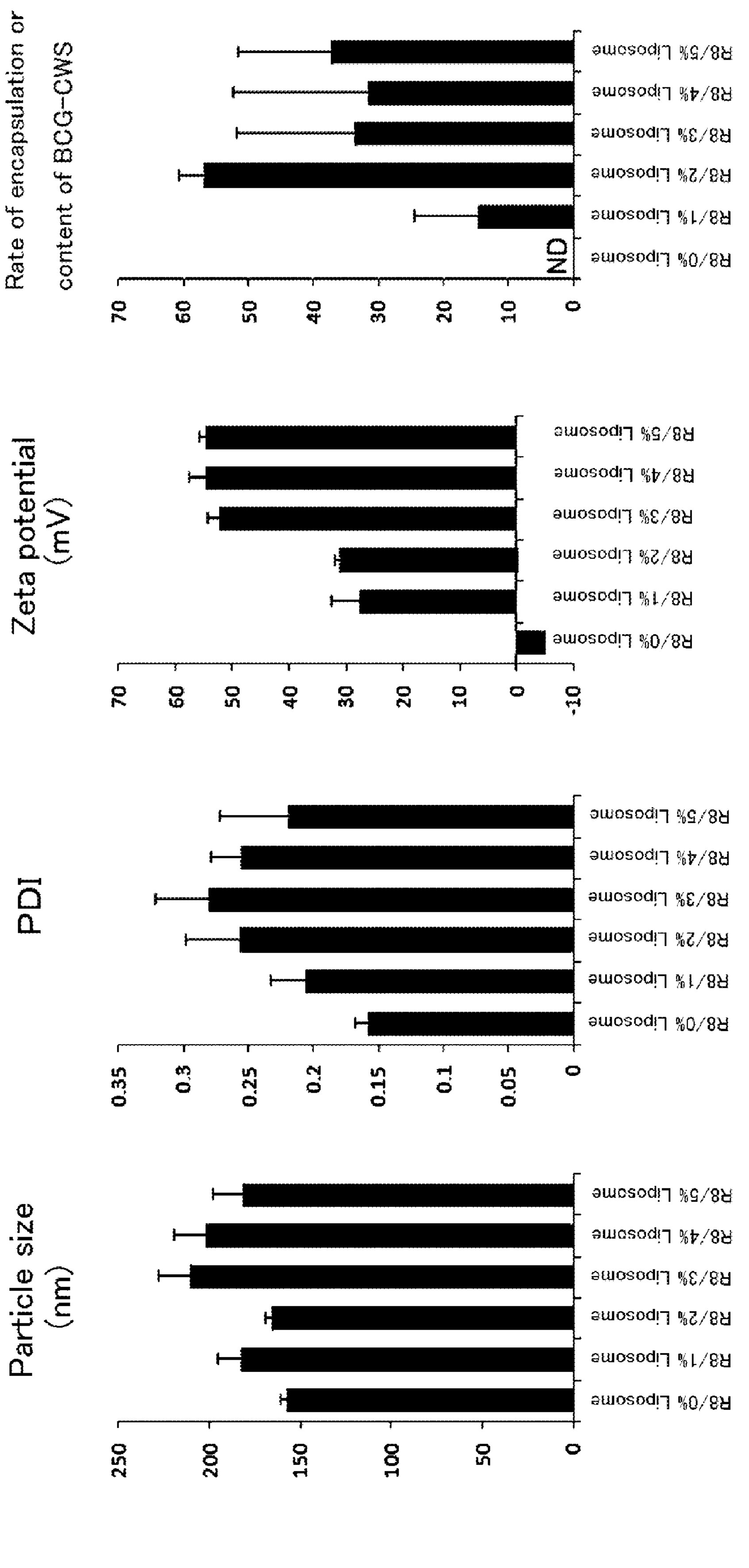
FIG. 6 is a diagram showing the particle size, PDI, zeta potential, and rate of encapsulation or content of BCG-CWS of each liposome comprising R8-bound lipid as a constituent lipid at a content of 0 to 5% and encapsulating BCG-CWS.

The particle size, PDI, zeta potential, and the rate of encapsulation or content of BCG-CWS were measured by the methods described in Example 2(1)[1-1] as to the R8/0 to 5% liposomes of Example 1(3). The results are shown in FIG. 6. As shown in FIG. 6, the particle size was substantially equivalent among the R8/0 to 5% liposomes, but was particularly small in the R8/2% liposome. These results showed that the particle size of the lipid membrane structure is particularly small when the content of the lipid bound with a peptide consisting of a plurality of arginine residues is 1% or larger and smaller than 3% with respect to the total amount of other constituent lipids.

Next, PDI was substantially equivalent among the R8/0 to 5% liposomes, but was particularly small in the R8/0% liposome. This seemed to be because the R8/0% liposome encapsulated no BCG-CWS, as mentioned later. Next, the zeta potential was a negative value (anionic) in the R8/0% liposome, but was a positive value (cationic) in all of the R8/1 to 5% liposomes. This seemed to be because the R8/0% liposome was free from the cationic substance STR-R8.

Finally, the rate of encapsulation or content of BCG-CWS was equal to or smaller than the detection limit (Not Detected; N.D.) in the R8/0% liposome, but was 15% or larger on average in all of the R8/1 to 5% liposomes. This means that: when the lipid membrane structure encapsulating no substance of interest had no R8-bound lipid as a constituent lipid, a lipid membrane structure having a particle size that permitted filtration sterilization and encapsulating a bacterial cell component was difficult to prepare; and by contrast, when the lipid membrane structure encapsulating no substance of interest had R8-bound lipid as a constituent lipid at a given concentration, a lipid membrane structure having a particle size that permitted filtration sterilization and encapsulating a bacterial cell component was successfully prepared. These results showed that even if the number of arginine residues in the peptide consisting of arginine residues is changed, a lipid membrane structure having a particle size that permits filtration sterilization and encapsulating a bacterial cell component can be prepared by changing the content of the lipid bound with a peptide consisting of a plurality of arginine residues and modifying the peptide.

(2) Microscopic Observation

HBS containing the liposome encapsulating BCG-CWS of Example 1(1) was prepared. This HBS was mixed with a 2% (v/v) aqueous tungstic acid solution and then added dropwise to a carbon vapor-deposited 400-mesh grid. Excessive water was removed, and the grid was dried in air, then observed at an acceleration voltage of 80 kV using a transmission electron microscopy JEM-1200EX (JEOL Ltd.), and photographed using a CCD cameral (Olympus Soft Imaging Solutions GmbH). In this observation under a transmission electron microscopy, BCG-CWS is observed as an irregular strand-like or sheet-like (uniform plane with almost no contrast) structure (Y. Uenishi et al., Journal of Microbiological Methods, Vol. 77, p. 139-144, 2009). This is presumably because BCG-CWS assumes a nonuniform structure such as a long chain structure or a folded structure in a solvent. On the other hand, the liposome has a uniform vesicle structure and as such, is probably observed as a concentric structure.

Figure 7:
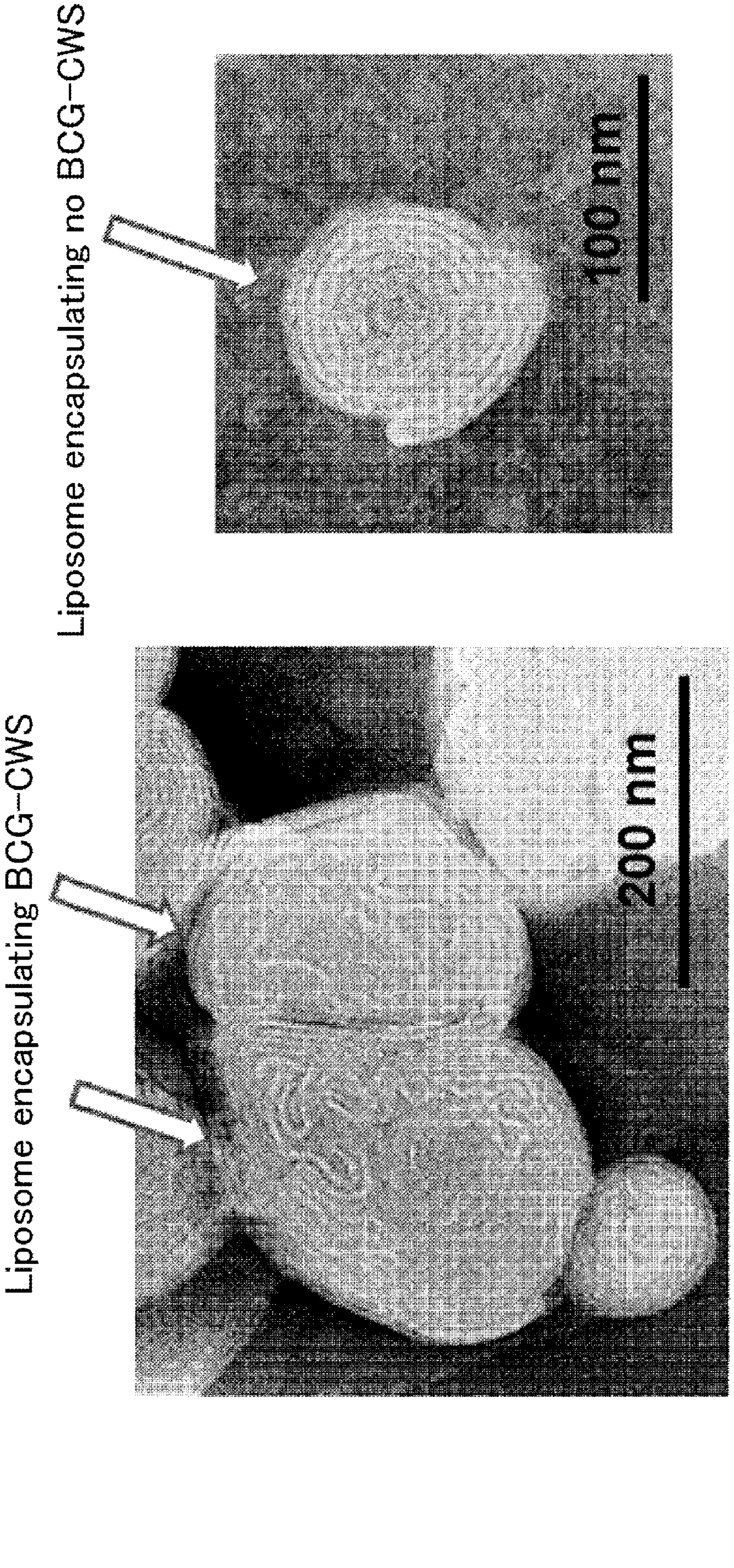
FIG. 7 shows observation images of a liposome encapsulating BCG-CWS and a liposome encapsulating no BCG-CWS under a transmission electron microscopy.

The photographing results are shown in FIG. 7. As shown in the left diagram of FIG. 7, for the liposome encapsulating BCG-CWS, irregular strand-like and sheet-like structures (which are probably of BCG-CWS) were observed within the concentric structure (which is probably of the liposome). These irregular strand-like and sheet-like structures were in a compactly folded particle form around which a gap indicating the presence of the solvent (pentane or HBS) was hardly observed. This revealed that the liposome encapsulating BCG-CWS encapsulated BCG-CWS and hardly encapsulated the solvent. As shown in the right diagram of FIG. 7, a liposome encapsulating no BCG-CWS was also observed in the HBS containing the liposome encapsulating BCG-CWS. In the liposome encapsulating no BCG-CWS, a morphological form was observed in which lipid membranes were densely packed up to the central portion of the concentric structure and few luminal portions were existed. This revealed that the methods shown in Examples 1(1)[1-1] to 1(1)[1-3], which involve distilling off the non-polar solvent under reduced pressure from the O/W emulsion, almost completely distill off the non-polar solvent present in the liposome lumen and produce a liposome hardly encapsulating the solvent.

These results showed that: the methods shown in Examples 1(1)[1-1] to 1(1)[1-3] can produce a lipid membrane structure encapsulating a substance of interest having dispersibility in a non-polar solvent; and the amount of the solvent encapsulated by this lipid membrane structure is very small.

(3) Amount of Polar Solvent Contained in Liposome; Study on Fluorescence Intensity Derived from Polar Solvent Contained in Liposome Each empty liposome was prepared by the method described in Example 1(1)[1-1], while a liposome encapsulating BCG-CWS was prepared by the methods described in Examples 1(1)[1-1] to 1(1)[1-3]. However, HBS present inside and outside each liposome was fluorescently stained by use of HBS containing 0.1 mmol/L calcein instead of HBS. Also, membrane filters having a pore size of 400 nm and a pore size of 200 nm were used to filter the empty liposomes. The empty liposome filtered through the former membrane filter was used as a large-diameter empty liposome, and the empty liposome filtered through the latter membrane filter was used as a small-diameter empty liposome. The particle size of each prepared liposome was measured using Zetasizer Nano ZS (Malvern Instruments Ltd.) and was consequently 248 nm for the large-diameter empty liposome, 160 nm for the small-diameter empty liposome, and 161 nm for the liposome encapsulating BCG-CWS.

Calcein is known to quench through complexation in the presence of cobalt chloride. On the basis of this fact, cobalt chloride was first added to the external solution of each liposome to eliminate the fluorescence of calcein in the external solution. Subsequently, the fluorescence intensity (relative fluorescence intensity: RFI) was measured at an excitation wavelength of 460 nm and a fluorescence wavelength of 550 nm using a fluorophotometer and used as fluorescence Intensity A. The fluorescence intensity A principally indicates the amount of fluorescence derived from HBS (HBS present in the lumen of the liposome and the gap in the lipid bilayer of the liposome) contained in the liposome. Next, the lipid membrane of the liposome was disrupted using 1% (v/v) TRITON-100 to eliminate the fluorescence of calcein in HBS contained in the liposome. Then, the fluorescence intensity was similarly measured and used as fluorescence intensity B. The fluorescence Intensity B Indicates the amount of background fluorescence after quenching of calcein inside and outside the liposome. Also, the total lipid amount (nmol) of the solution in which the liposome was contained was measured using a phospholipid quantification kit (Wako Pure Chemical Industries, Ltd.). On the basis of the measurement results, the fluorescence intensity truly derived from HBS contained in the liposome (fluorescence intensity derived from contained HBS) was calculated according to the following expression 2:

Fluorescence intensity derived from contained HBS (RFI)=Fluorescence intensity *A*−Fluorescence intensity *B*. Expression 2;

Next, the value of the fluorescence intensity derived from contained HBS was divided by the total lipid amount to determine fluorescence intensity derived from contained HBS per nmol of lipid (RFI/nmol). This experiment of Example 2(3) was conducted 4 times to determine a mean of RFI/nmol and standard deviation. RFI/nmol of the liposome encapsulating BCG-CWS was subjected to a significance test (two-way repeated measures ANOVA, Tukey-Kramer method) vs. the large-diameter empty liposome and the small-diameter empty liposome. The results are shown in FIG. 8.

Figure 8:
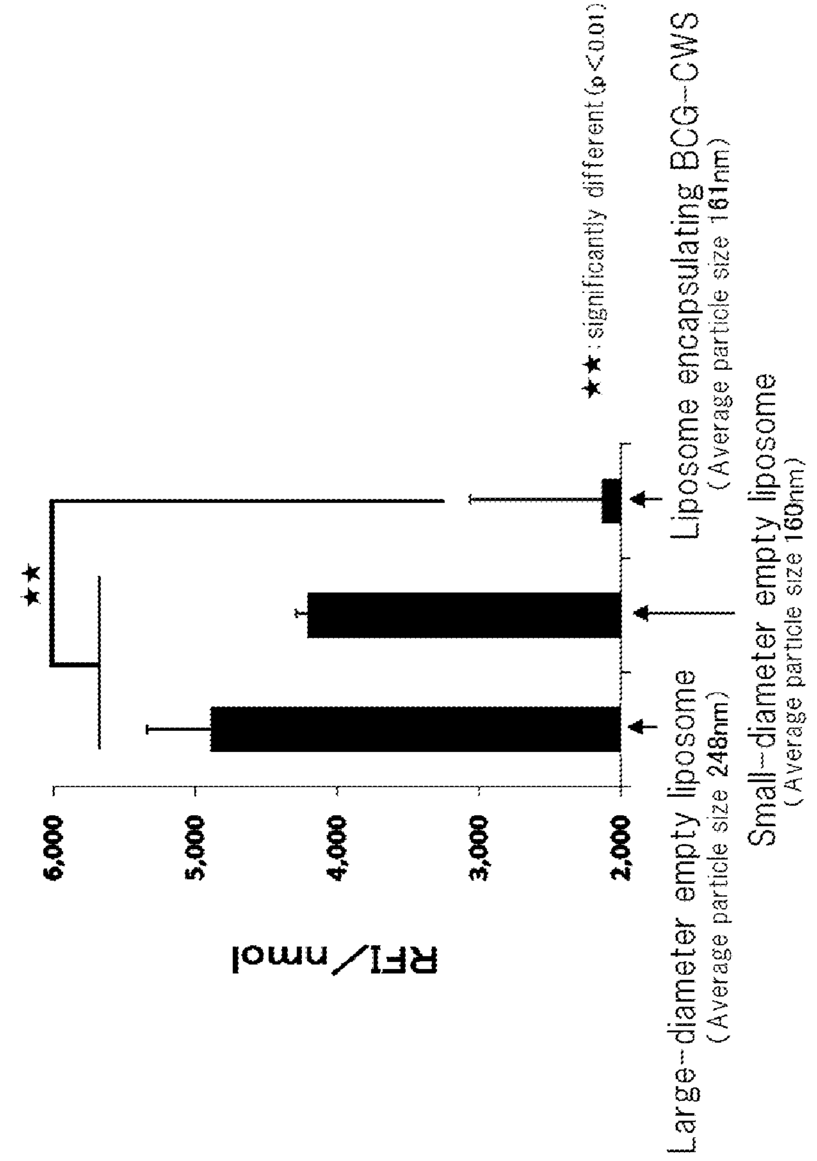
FIG. 8 is a diagram showing internal solution-derived fluorescence intensity (RFI/nmol) per nmol of lipid in a large-diameter empty liposome, a small-diameter empty liposome, and a liposome encapsulating BCG-CWS.

As shown in FIG. 8, RFI/nmol of the liposome encapsulating BCG-CWS was significantly small as compared with the large-diameter empty liposome and the small-diameter empty liposome. RFI/nmol of the liposome encapsulating BCG-CWS was smaller than 3500 even in consideration of the range of the standard deviation. This revealed that the amount of HBS contained in the liposome encapsulating BCG-CWS was remarkably small as compared with the empty liposome having a larger particle size and even the empty liposome having almost the same particle size. These results showed that the amount of the polar solvent contained in the lipid membrane structure prepared by the methods shown in Examples 1(1)[1-1] to 1(1)[1-3] is remarkably small. These results also showed that when the polar solvent contained in the lipid membrane structure is 10 mmol/L HBS containing calcein at a final concentration of 0.1 mmol/L and having a pH of 7.4, the fluorescence intensity of calcein derived from the polar solvent contained in the lipid membrane structure is less than 3500 per nmol of the constituent lipid of the lipid membrane structure in the measurement at an excitation wavelength of 460 nm and a fluorescence wavelength of 550 nm.

(4) Amount of Polar Solvent Contained in Liposome; Study Based on Reduction in Fluorescence Intensity When the liposome is disrupted by TRITON X-100, the external solution of the liposome is diluted with the polar solvent contained in the liposome to decrease the concentration of calcein, resulting in reduction in fluorescence intensity. On the basis of this fact, the amount of the polar solvent contained in each liposome was measured. Specifically, an empty liposome was prepared by the method described in Example 1(1)[1-1], while a liposome encapsulating BCG-CWS was prepared by the methods described in Examples 1(1)[1-1] to 1(1)[1-3]. To 10 μL of HBS containing each liposome, 970 μL of HBS and 20 μL of a 0.1 mmol/L calcein solution were added. This mixture was halved into 500 μL. One of the portions was supplemented with 5 μL of 10% (v/v) TRITON X-100 (final concentration: 0.1% (v/v)) and used as a solution B. The other portion was supplemented with 5 μL of HBS and used as a solution A. Approximately 300 μL aliquots of the solution A and the solution B were each added to 100 kDa Microcon (EMD Millipore) and ultrafiltered by centrifugation for 10 minutes under conditions of 5000 rpm and 4° C. From the non-ultrafiltered samples and the ultrafiltered samples, 100 μL aliquots were separated, and the fluorescence intensity was measured.

As a result, the fluorescence intensity was smaller in the solution B than in the solution A. The degree of reduction in fluorescence intensity in the solution B compared with the solution A was smaller in the liposome encapsulating BCG-CWS than in the empty liposome. These results showed that the amount of the polar solvent contained in the lipid membrane structure prepared by the methods shown in Examples 1(1)[1-1] to 1(1)[1-3] is remarkably small.

(5) Amount of Polar Solvent Contained in Liposome; Study Based on Weight Measurement A liposome encapsulating BCG-CWS was prepared by the methods described in Examples 1(1)[1-1] to 1(1)[1-3]. Subsequently, the liposome was freeze-dried to obtain a freeze-dried product. The weight of the freeze-dried product was measured. Then, the freeze-dried product was resuspended by the addition of 1 mL of DDW to prepare a resuspended liposome. Subsequently, the resuspended liposome was separated from the external aqueous layer by centrifugation for 30 minutes under conditions of 43000 rpm and 4° C. Then, the wet weight of the resuspended liposome was measured. Also, the lipid concentration thereof was measured using a phospholipid quantification kit (Wako Pure Chemical Industries, Ltd.). The wet weight of the resuspended liposome was corrected on the basis of the measurement results. Subsequently, the weight of the aqueous solution contained in the liposome encapsulating BCG-CWS was determined according to the following expression 3:

Corrected wet weight of the resuspended liposome−Weight of the freeze-dried product. Expression 3;

<Example 3> Cellular Uptake (1) Preparation of Liposome

A liposome encapsulating BCG-CWS was prepared by the methods described in Examples 1(1)[1-1] to 1(1)[1-3], while a liposome containing BCG-CWS in a lipid membrane was prepared by the method described in Example 1(4). However, nitro-2-1,3-benzoxadiazol-4-yl (NBD)-bound DOPE (NBD-labeled DOPE; Avanti Polar Lipids, Inc.) was added at a molar ratio of 1% with respect to the total amount of other constituent lipids to each of the lipid chloroform solution and the mixed lipid solution of BCG to label the surface of each liposome with NBD.

(2) Fluorescent Observation

Mouse bladder cancer cell line MBT-2 cells (RIKEN, Japan) were inoculated at a density of $2\times10^5$ cells to a plate and cultured at 37° C. for 1 day in a 5% (v/v) $CO_2$ atmosphere using an RPMI1640 medium supplemented with 10% fetal calf serum (FCS) (FCS-supplemented RPMI medium). After removal of the medium, the cells were washed with 1 mL of phosphate-buffered saline (PBS). Subsequently, 1 mL of an RPMI1640 medium containing the liposome encapsulating BCG-CWS or the liposome containing BCG-CWS in a lipid membrane in Example 3(1) at a total lipid concentration of 75 μmol/L was added to the cells. The liposome was taken up into the MBT-2 cells by incubation for 1 hour under the same conditions as above. After removal of the medium, the cells were washed two repetitive times with 1 mL of PBS containing 20 U/mL heparin and then washed once with 1 mL of an FCS-supplemented RPMI medium. Subsequently, 1 mL of an FCS-supplemented RPMI medium was added to the cells, which were then incubated for 45 minutes under the same conditions as above. Next, 5 μL of 100 μmol/L LysoTracker Red was added to the cells, which were further incubated for 15 minutes to stain the acidic compartments of the MBT-2 cells. Then, the cells were washed two repetitive times with 1 mL of an FCS-supplemented RPMI medium. Then, 1 mL of an FCS-supplemented RPMI medium was added thereto, and the fluorescence of NBD (green) and LysoTracker Red (red) was observed under a confocal laser scanning microscope (LSM510; Carl Zeiss AG). The results are shown in FIG. 9.

Figure 9:
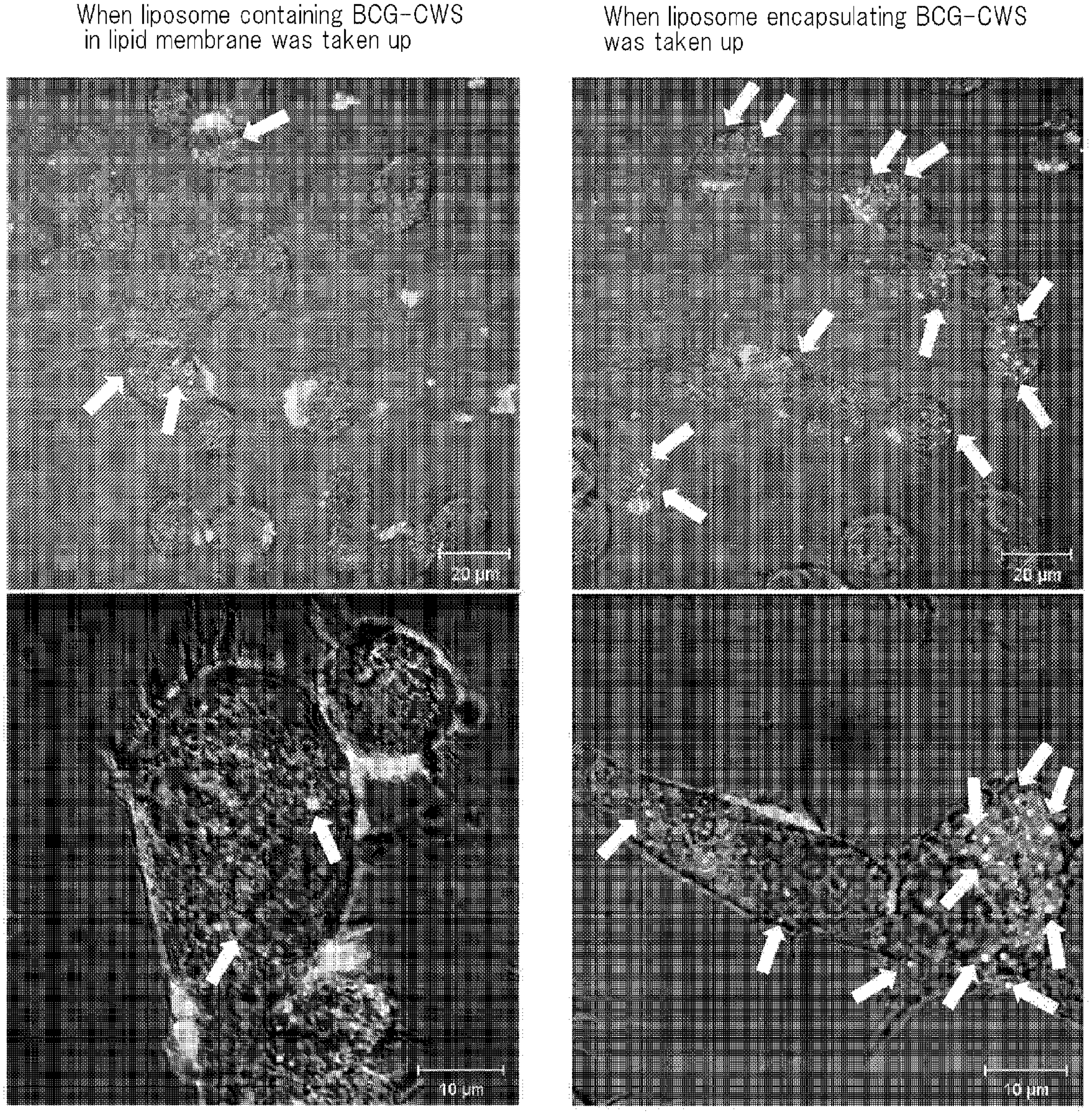
FIG. 9 is a diagram showing the positions of each liposome (green) and an acidic compartment (red) in MBT-2 cells in which an NBD-labeled liposome containing BCG-CWS in a lipid membrane or an NBD-labeled liposome encapsulating BCG-CWS was taken up. In the diagram, the arrows depict main sites where yellow fluorescence that indicates the overlap between green and red was observed.

As shown in FIG. 9, green fluorescence and yellow fluorescence indicating the overlap between green and red were observed within the MBT-2 cells in which the liposome containing BCG-CWS in a lipid membrane or the liposome encapsulating BCG-CWS was taken up. The number of sites where the yellow fluorescence was observed was larger when the liposome encapsulating BCG-CWS was taken up than when the liposome containing BCG-CWS in a lipid membrane was taken up. These results revealed that the liposome encapsulating BCG-CWS is efficiently taken up into the MBT-2 cells.

(3) FACS Assay

A liposome encapsulating BCG-CWS was taken up into MBT-2 cells by the method described in Example 3(2), followed by the washing of the cells. However, the incubation time after the addition of the liposome was set to 1 hour instead of 2 hours. Subsequently, 1 mL of an FCS-supplemented RPMI medium was added to the cells, which were then incubated for 1 hour under the same conditions as above and used as a sample group. Also, the same number of MBT-2 cells thereas in which no liposome encapsulating BCG-CWS was taken up was used as a control group. The fluorescence intensity of NBD and the number of cells were measured for the cells of the sample group and the control group using flow cytometry (FACSCalibur; Nippon Becton Dickinson Company Ltd.). The overall fluorescence intensity of the sample group was subjected to a significance test (unpaired t-test) vs. the overall fluorescence intensity of the control group. The overall fluorescence intensity of each group is shown in the left diagram of FIG. 10, and the relationship between the fluorescence intensity of each cell and the number of cells is shown in the right diagram of FIG. 10.

Figure 10:
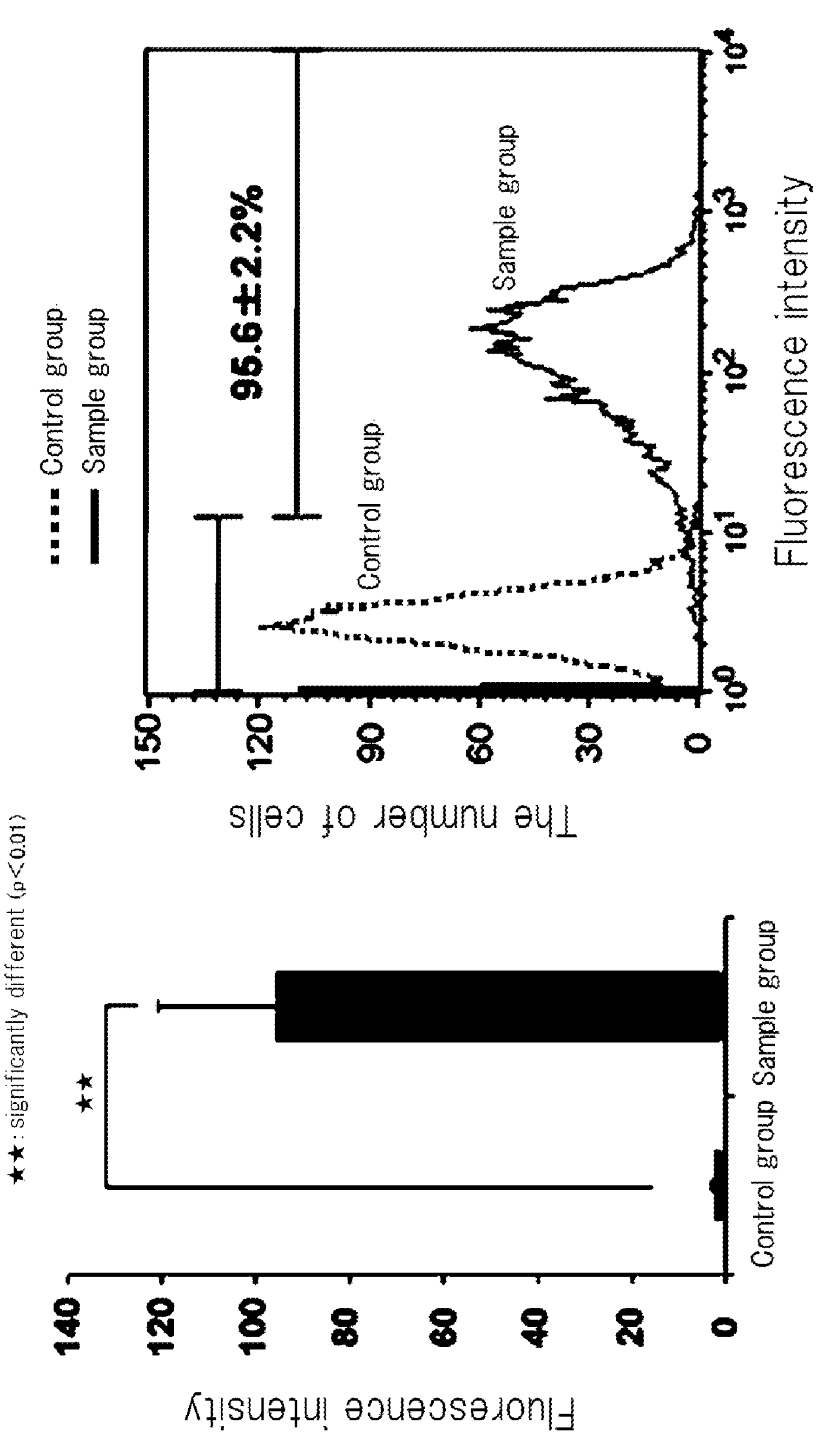
FIG. 10 is a diagram showing the overall fluorescence intensity of each group (left diagram) and the relationship between the fluorescence intensity of each cell and the number of cells (right diagram) in an MBT-2 cell group in which an NBD-labeled liposome encapsulating BCG-CWS was taken up (sample group) and an MBT-2 cell group in which no liposome was taken up (control group).

As shown in the left diagram of FIG. 10, the overall fluorescence intensity of the sample group was significantly larger than the overall fluorescence intensity of the control group. As shown in the right diagram of FIG. 10, a large number of cells having large fluorescence intensity were detected in the sample group compared with the control group. The number of cells having large fluorescence intensity as compared with the cells of the control group, among the cells of the sample group, was converted to a percentage and was consequently 96.5±2.2%. These results demonstrated that a large number of cells in the sample group took up the liposome encapsulating BCG-CWS.

These results of Examples 3(1) and 3(2) demonstrated that the lipid membrane structure which has a particle size that permits filtration sterilization, comprises a lipid bound with a peptide consisting of a plurality of arginine residues as a constituent lipid, and encapsulates a bacterial cell component having dispersibility in a non-polar solvent is efficiently taken up into cancer cells.

<Example 4> Anticancer Effect (1) Effect on Transplanted Cancer Cell

[1-1] Tumor Volume

Eight-week-old female C3H/HeN mice (Japan SLC, Inc.) were divided into 6 groups (A to F) each involving 4 to 6 mice. MBT-2 cells were cultured at 37° C. in a 5% (v/v) $CO_2$ atmosphere using an FCS-supplemented RPMI medium. Then, after removal of the medium, $3.5\times10^6$ cells were suspended in PBS to prepare a cell suspension. The cell suspension and each liposome given below were placed in a microtube and mixed to obtain a transplant solution. The transplant solution was subcutaneously injected to the right abdomens of the mice in each group using a 26 G needle and a tuberculin syringe to transplant the MBT-2 cells to the mice. Then, the mice in each group were reared for 25 days. The rearing was carried out under conditions of standard temperature and humidity and 12-hour light/12-hour dark cycles. In this period, the mice freely took feed and drinking water. On days 14, 19, 21, and 25 after the transplantation, one to several mice were randomly selected from each group, and the major axis and the minor axis of a tumor at the transplantation site were measured using a vernier caliper. In this context, the tumor is easily distinguishable by visual observation as a raised cell mass. Subsequently, on the basis of the results of measuring the major axis and the minor axis, the tumor volume was calculated according to the following expression 4:

$$\text{Tumor volume (mm}^3\text{)}=0.52\times\text{Major axis}\times(\text{Minor axis})^2 \qquad \text{Expression 4;}$$

Figure 11:
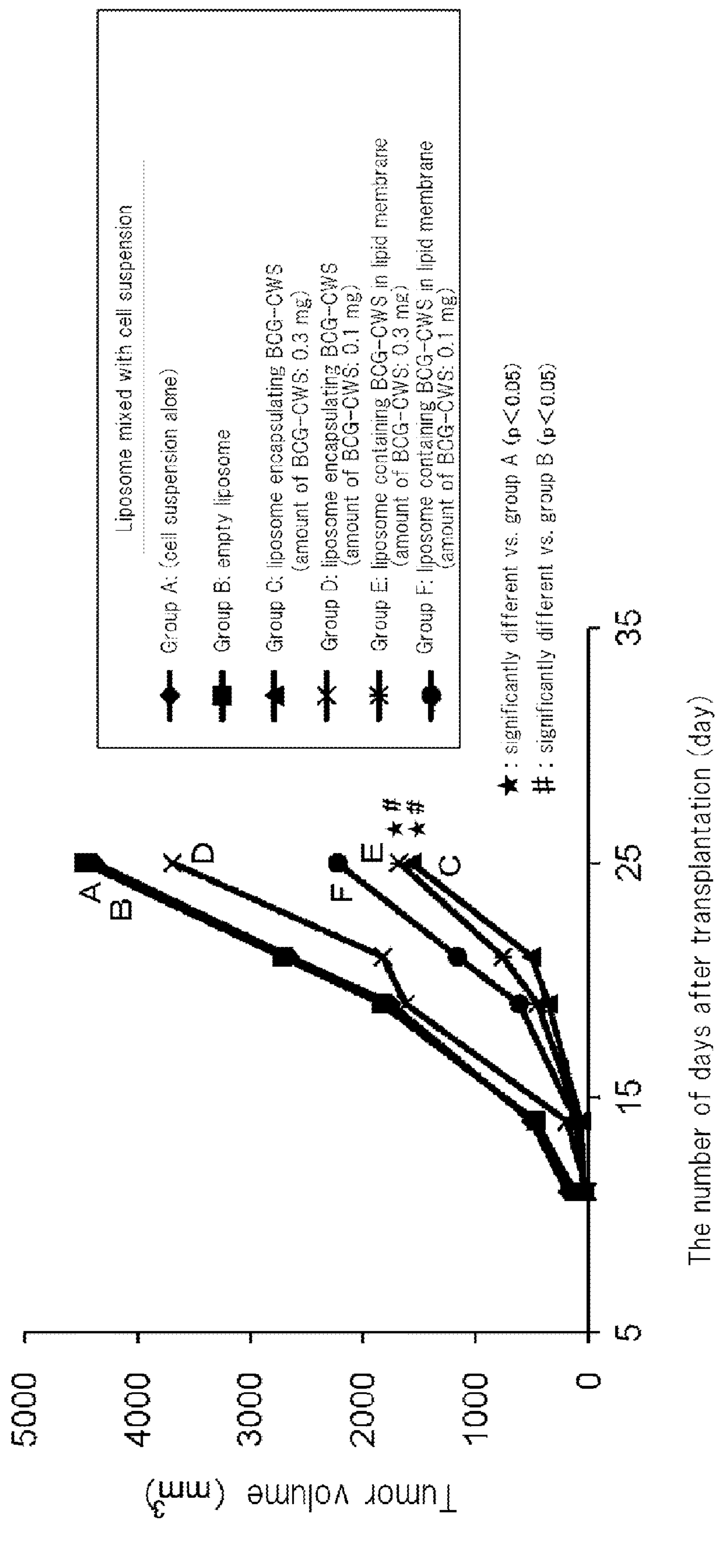
FIG. 11 is a diagram showing the tumor volumes of mice that received transplants of MBT-2 cells alone (group A) and mice that received transplants of MBT-2 cells as well as each administered liposome (groups B to F).

The tumor volumes of the groups C to F on day 25 after the transplantation were subjected to a significance test (two-way repeated measures ANOVA, Dunnett's method) vs. the groups A and B. The results are shown in FIG. 11.

"Liposome Mixed with Cell Suspension"

Group A (n=5): (cell suspension alone)

Group B (n=5): empty liposome of Example 1(1)[1-1] (amount of lipid: 2.56 mg)

Group C (n=5): liposome encapsulating BCG-CWS of Example 1(1)[1-3] (amount of BCG-CWS: 0.3 mg, amount of lipid: 2.56 mg)

Group D (n=4): liposome encapsulating BCG-CWS of Example 1(1)[1-3] (amount of BCG-CWS: 0.1 mg, amount of lipid: 0.85 mg)

Group E (n=6): liposome containing BCG-CWS in lipid membrane of Example 1(4) (amount of BCG-CWS: 0.3 mg, amount of lipid: 2.56 mg)

Group F (n=4): liposome containing BCG-CWS in lipid membrane of Example 1(4) (amount of BCG-CWS: 0.1 mg, amount of lipid: 0.85 mg)

As shown in FIG. 11, the tumor volume on day 25 after the transplantation tended to be small in the groups D and F compared with the groups A and B and was significantly small in the groups C and E. These results revealed that the administration of the liposome encapsulating BCG-CWS in addition to the transplantation of MBT-2 cells suppresses the engraftment or growth of the transplanted MBT-2 cells.

[1-2] Survival Rate

Figure 12:
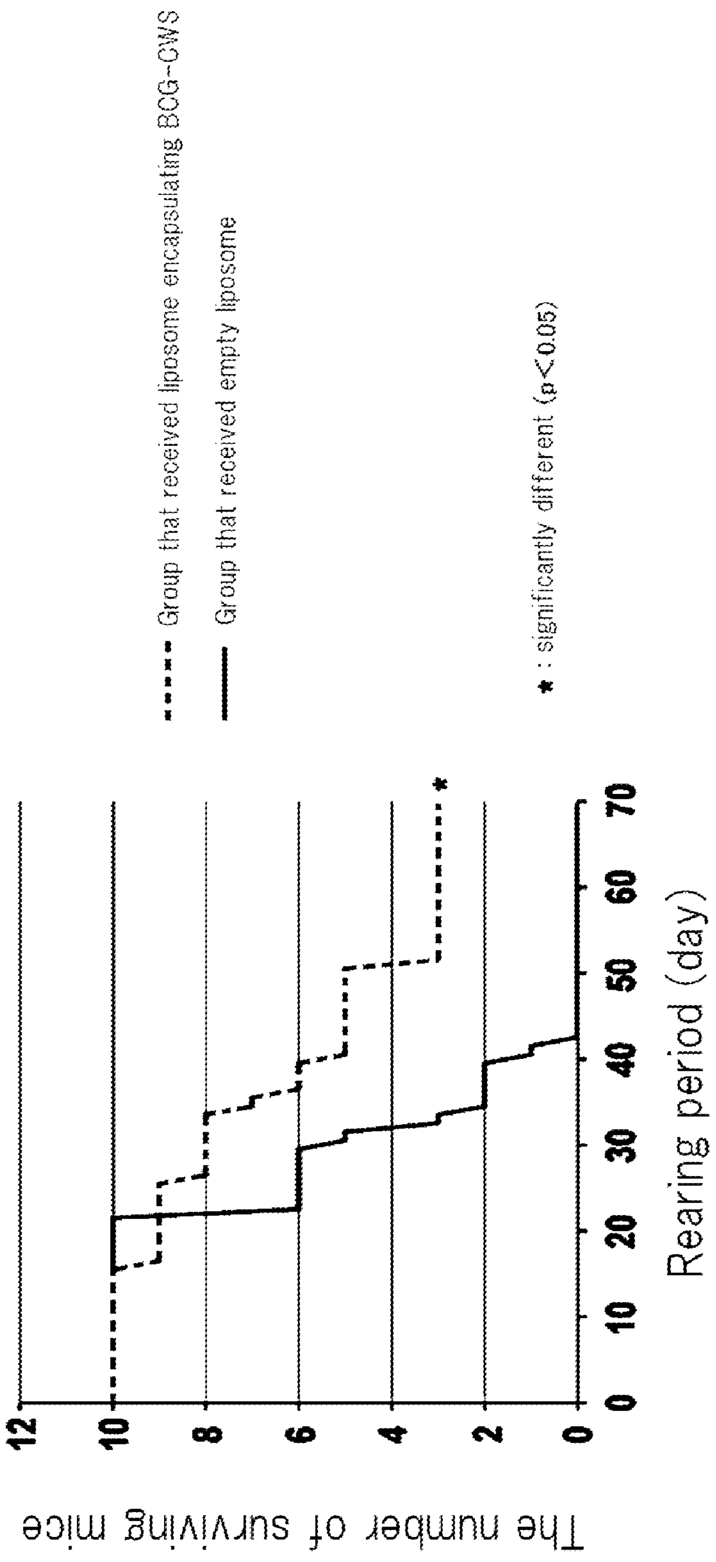
FIG. 12 is a diagram showing the number of surviving mice among mice that received transplants of MBT-2 cells as well as an administered liposome encapsulating BCG-CWS or an administered empty liposome.

Eight-week-old female C3H/HeN mice (Japan SLC, Inc.) were divided into 2 groups (an administration group of the liposome encapsulating BCG-CWS and an administration group of the empty liposome) each involving 10 mice. MBT-2 cells were transplanted to the mice in each group by the method described in Example 4(1)[1-1]. The mice were reared for approximately 60 days, and the number of surviving mice was counted. However, each liposome mixed with the cell suspension for the transplant solution was as described below. The number of surviving mice in the administration group of the liposome encapsulating BCG-CWS was subjected to a significance test (logrank test) vs. the administration group of the empty liposome. The results are shown in FIG. 12. As shown in FIG. 12, the number of surviving mice in the administration group of the liposome encapsulating BCG-CWS was significantly large as compared with the administration group of the empty liposome. These results revealed that the administration of the liposome encapsulating BCG-CWS in addition to the transplantation of MBT-2 cells elevates the survival rate.

"Liposome Mixed with Cell Suspension"

Administration group of the liposome encapsulating BCG-CWS: liposome encapsulating BCG-CWS of Example 1(1)[1-3] (amount of BCG-CWS: 0.3 mg, amount of lipid: 2.56 mg)

Administration group of the empty liposome: empty liposome of Example 1(1)[1-1] (amount of lipid: 2.56 mg)

[1-3] Area of Tumor Tissue and the Number of Leukocytes

MBT-2 cells were cultured at 37° C. for 1 hour in a 5% (v/v) $CO_2$ atmosphere using an FCS-supplemented RPMI medium supplemented with the liposome encapsulating BCG-CWS of Example 1(1)[1-3] (amount of BCG-CWS: 0.1 mg, amount of lipid: 0.85 mg) with respect to $1.0\times10^6$ cells. Then, the cells were washed with PBS containing 20 U/mL heparin to remove a liposome that was not taken up into the cells. The MBT-2 cells in which the liposome encapsulating BCG-CWS was taken up were obtained by this treatment and used as lipo-incorporated cells.

Four 8-week-old female C3H/HeN mice (Japan SLC, Inc.) were prepared and designated as mice a to d, respectively. As described below, $1.0\times10^6$ MBT-2 cells or lipo-incorporated cells were transplanted to each mouse, and each liposome was administered thereto. The mice were reared for 10 days. The culture and transplantation of the MBT-2 cells, the administration of the liposome, and the culture of the mice were carried out in the same way as the methods described in Example 4(1)[1-1]. Then, tumor tissues were collected from each mouse and embedded in paraffin according to a routine method. Then, sections of approximately 3 μm in thickness were prepared and subjected to hematoxylin-eosin staining and Giemsa staining. The images of the hematoxylin-eosin-stained sections were analyzed using image analysis software NIH Image Ver. 1.44p (Wayne Rasband, National Institute of Health, USA) to measure the total area of tumor tissues, the area of viable tumor tissues, the area of dead tumor tissues, and the ratio of dead cells (%). Also, the numbers of various leukocytes in the tumor tissues were measured by observation in the high power field (HPF).

Mouse a: subcutaneous injection of a transplant solution of the MBT-2 cells mixed with the empty liposome of Example 1(1)[1-1] (amount of lipid: 0.85 mg).

Mouse b: subcutaneous injection of a transplant solution of the MBT-2 cells mixed with the liposome encapsulating BCG-CWS of Example 1(1)[1-3] (amount of BCG-CWS: 0.1 mg, amount of lipid: 0.85 mg).

Mouse c: subcutaneous injection of a cell suspension containing the lipo-incorporated cells.

Mouse d: subcutaneous injection of a cell suspension containing the MBT-2 cells and PBS containing the liposome encapsulating BCG-CWS of Example 1(1)[1-3] (amount of BCG-CWS: 0.1 mg, amount of lipid: 0.85 mg) at sites distant from each other.

Figure 13:
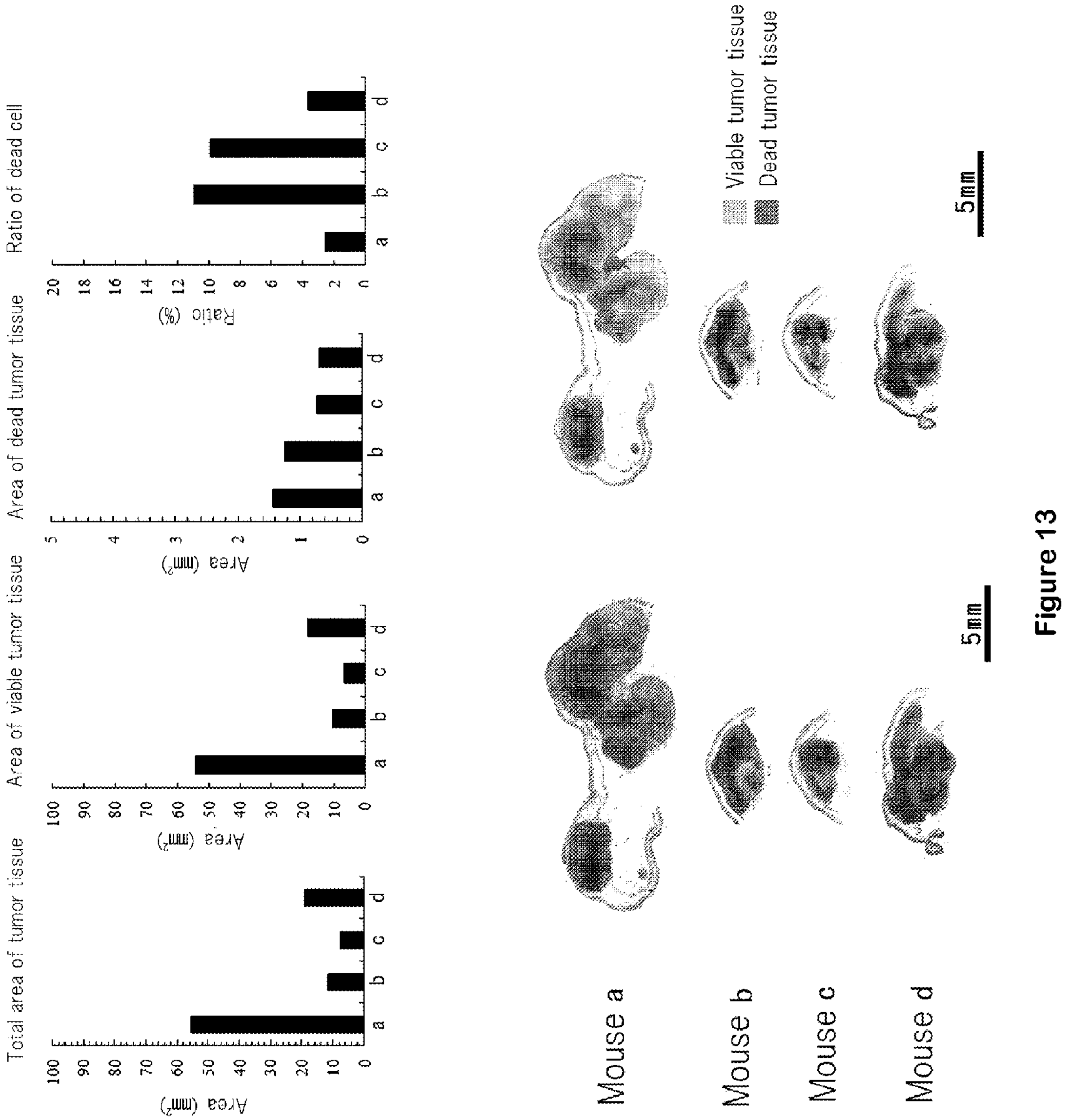
FIG. 13 is a diagram showing the total area of tumor tissues, the area of viable tumor tissues, the area of dead tumor tissues, and the ratio of dead cells (%) in upper bar graphs wherein a represents a mouse a given subcutaneous injection of MBT-2 cells mixed with an empty liposome; b represents a mouse b given subcutaneous injection of MBT-2 cells mixed with a liposome encapsulating BCG-CWS; c represents a mouse c given subcutaneous injection of MBT-2 cells in which a liposome encapsulating BCG-CWS was taken up; and d represents a mouse d given subcutaneous injection of MBT-2 cells and a liposome encapsulating BCG-CWS at sites distant from each other. The lower left diagrams are photographs showing hematoxylin-eosin-stained tumor tissue sections of the mice a to d. The lower right diagrams are diagrams showing viable tumor tissues and dead tumor tissues in the hematoxylin-eosin stain images shown in the left diagrams.

The results of measuring the total area of tumor tissues, the area of viable tumor tissues, the area of dead tumor tissues, and the ratio of dead cells (%) are shown in FIG. 13. As shown in FIG. 13, in the mice b to d compared with the mouse a, the total area of tumor tissues and the area of viable tumor tissues were remarkably small; the area of dead tumor tissues was at almost the same level, albeit small; and the ratio of dead cells was large. These results revealed that the administration of the liposome encapsulating BCG-CWS in addition to the transplantation of MBT-2 cells suppresses the enlargement of tumor tissues derived from the transplanted MBT-2 cells and maintains or promotes the cell death in the tumor tissues.

In the mice b and c compared even with the mouse d, the total area of tumor tissues and the area of viable tumor tissues were small, and the ratio of dead cells was remarkably large. These results revealed that the transplantation of the mixture of the liposome encapsulating BCG-CWS with the MBT-2 cells or the transplantation of the MBT-2 cells in which the liposome encapsulating BCG-CWS was taken up was more effective for suppressing the enlargement of tumor tissues or for maintaining or promoting the cell death in the tumor tissues.

Figure 14:
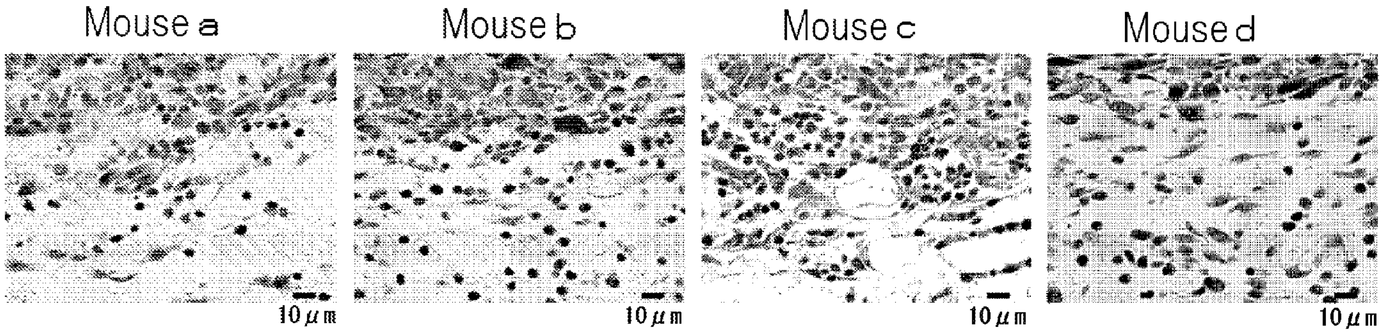
FIG. 14 has two diagrams. The upper diagram is a diagram showing the numbers and ratios of various leukocytes in the tumor tissues of the mice a to d. The lower diagrams are photographs showing Giemsa-stained tumor tissue sections of the mice a to d.

The results of measuring the numbers and ratios of various leukocytes in the tumor tissues are shown in FIG. 14. In the lower photographs of FIG. 14, the cells having a round nucleus with dark color are lymphocytes. As shown in FIG. 14, the mice b to d had large numbers of macrophages, lymphocytes, neutrophils, eosinophils, and mast cells and a large total number of leukocytes as compared with the mouse a. As for the rate of increase in various leukocytes, lymphocytes were particularly increased in the mice b to d compared with the mouse a. These results revealed that the administration of the liposome encapsulating BCG-CWS in addition to the transplantation of MBT-2 cells promotes the infiltration of immunocytes, particularly, the infiltration of lymphocytes, into tumor tissues derived from the transplanted MBT-2 cells.

The mice b and c compared even with the mouse d had large numbers of lymphocytes, neutrophils, eosinophils, and mast cells and a large total number of leukocytes in the tumor tissues and exhibited a large rate of increase in lymphocytes. These results revealed that the transplantation of the mixture of the liposome encapsulating BCG-CWS with the MBT-2 cells or the transplantation of the MBT-2 cells in which the liposome encapsulating BCG-CWS was taken up was more effective for infiltrating immunocytes into the tumor tissues.

(2) Effect on Bladder Cancer Rat Model

Fifty four 6-week-old male F344/DuCrlCrlj rats (Charles River Laboratories Japan, Inc.) were prepared. These rats were reared for 8 weeks while freely taking drinking water containing 0.05% of a carcinogen N-butyl-N-(4-hydroxybutyl)nitrosamine and feed containing 5% of a cancer promoter sodium ascorbate so that bladder cancer was induced therein to prepare bladder cancer rat models. The bladder cancer rat models were divided into 6 groups (G to L) each involving 9 rats and reared while intravesically given a total of 8 doses (at 1-week intervals) of a phosphate buffer solution containing each liposome given below. For the intravesical administration, each rat was placed supine under light ether anesthesia and allowed to urinate by compression. Then, a cannula catheter attached with 24 G× ¾ inch indwelling needle was inserted through the external urethral opening and used in the administration. In the rearing period during the liposome dosing period, the rats freely took usual feed and drinking water and were reared under conditions of standard temperature and humidity and 12-hour light/12-hour dark cycles.

“Administered Liposome (Single Dose is Shown in the Parentheses < >)”

Group G: (non-administered)

Group H: empty liposome of Example 1(1)[1-1]<amount of lipid (in terms of the amount of BCG-CWS): 0.1 mg/1 mL×body weight of each rat individual (kg)>

Group I: liposome encapsulating BCG-CWS of Example 1(1)[1-3]<amount of BCG-CWS: 0.1 mg/1 mL×body weight of each rat individual (kg)>

Group J: liposome encapsulating BCG-CWS of Example 1(1)[1-3]<amount of BCG-CWS: 0.03 mg/1 mL×body weight of each rat individual (kg)>

Group K: liposome containing BCG-CWS in a lipid membrane of Example 1(4)<amount of BCG-CWS: 0.1 mg/1 mL×body weight of each rat individual (kg)>

Group L: liposome containing BCG-CWS in a lipid membrane of Example 1(4)<amount of BCG-CWS: 0.03 mg/1 mL×body weight of each rat individual (kg)>

Each rat was reared for 1 week after the final administration and then dissected to excise its bladder, which was fixed by dipping 10% neutral buffered formalin. The bladder thus fixed was divided into sagittal sections, and the weight was measured using an electronic balance. In this context, the bladder weight is considered to get larger with the progression of bladder cancer. Then, the bladder was divided into 4 portions and embedded in paraffin to prepare sections of approximately 3 μm in thickness, followed by hematoxylin-eosin staining. The stained sections were observed to count the number of epithelial lesions (tumors). The length of the bladder basement membrane was measured by image analysis. On the basis of the measurement results, the number of epithelial lesions (tumors) per 10 cm of the bladder basement membrane was calculated. Subsequently, the bladder weights and the numbers of epithelial lesions (tumors) per 10 cm of the bladder basement membrane in the groups I to L were subjected to a significance test (one-way analysis of variance, Dunnett’s method) vs. the groups G and H. The tumor volumes of the groups G to J were also measured by the method described in Example 4(1)[1-1]. The bladder was excised and cleaved into two. Digital photographs were taken on the mucosa side. Then, binarized images of tumor lesions were prepared to measure the number of lesions and the tumor volume.

Figure 15:
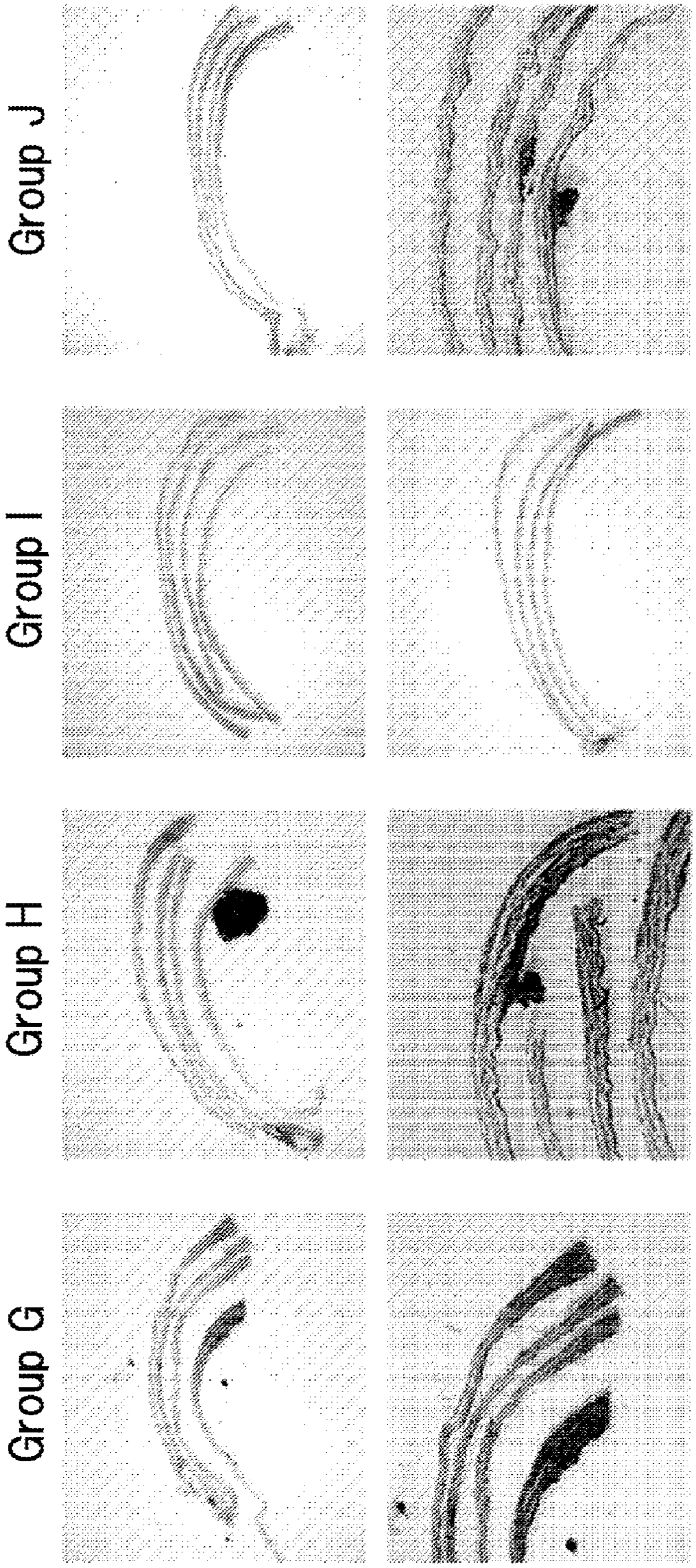
FIG. 15 is a diagram showing bladder sections of non-administered bladder cancer rat models (group G) and bladder cancer rat models that received each intravesically administered liposome (groups H to J).

The tumor volumes of the groups G, I, and J were subjected to a significance test (one-way analysis of variance, Dunnett’s method) vs. the group H. The bladder sections of the groups G to J are shown in FIG. 15. The bladder weights and the numbers of epithelial lesions (tumors) per 10 cm of the bladder basement membrane in the groups G to L and the results of measuring the tumor volumes of the groups G to J are shown in FIG. 16.

Figure 16:
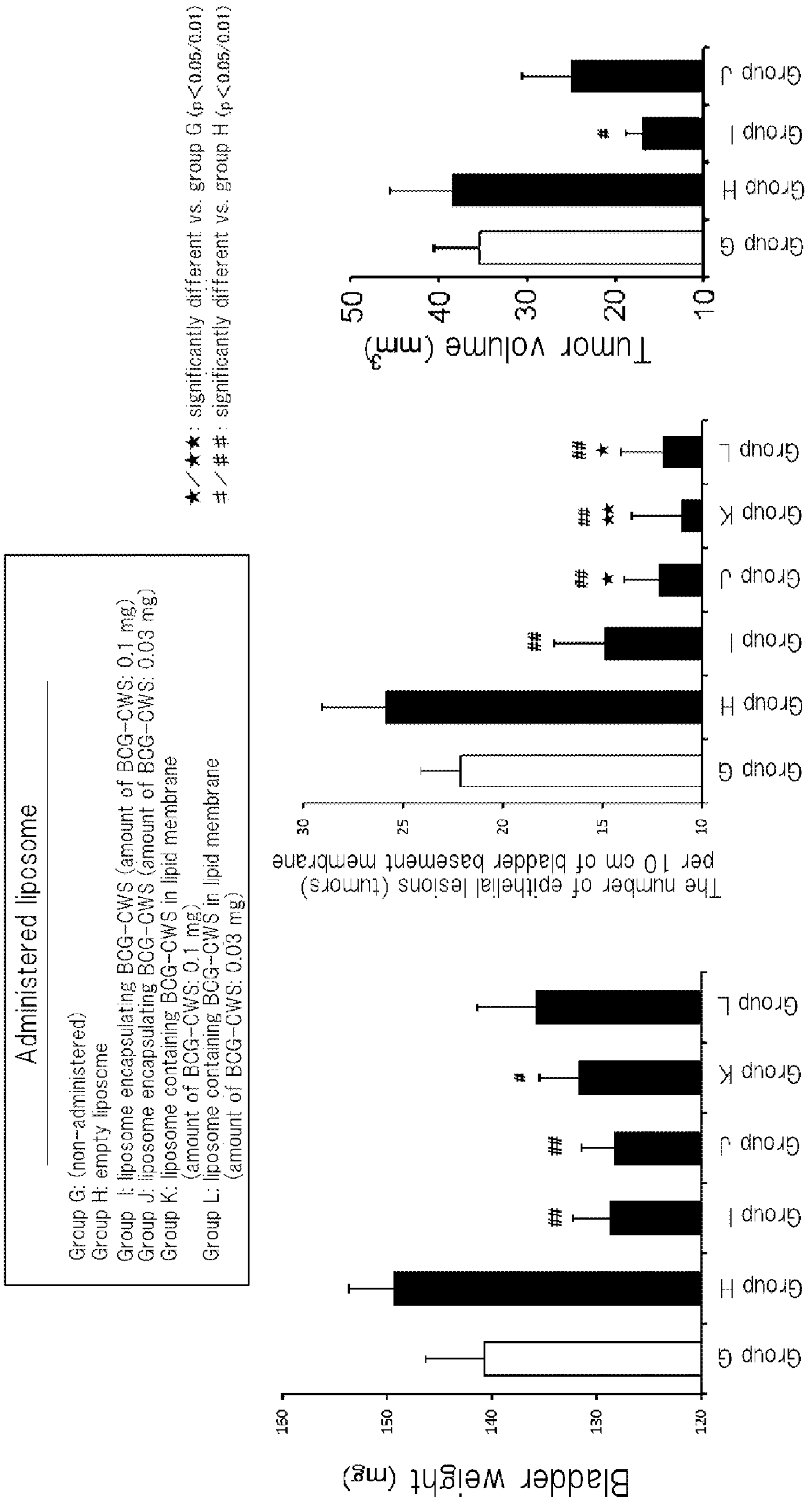
FIG. 16 is a diagram showing the bladder weights, the number of epithelial lesions (tumors) per 10 cm of the bladder basement membrane, and tumor volumes of non-administered bladder cancer rat models (group G) and bladder cancer rat models that received each intravesically administered liposome (groups H to L).

As shown in the left diagram of FIG. 16, the bladder weight was smallest in the groups I and J among the groups G to L. The bladder weight was significantly small in the groups I to K compared with the group H. These results revealed that the administration of the liposome encapsulating BCG-CWS to a bladder cancer rat model decreases the bladder weight or prevents increase in the bladder weight. As shown in FIG. 15, the number of epithelial lesions (tumors) in the bladder was remarkably small in the groups I and J compared with the groups G and H. As shown in the central diagram of FIG. 16, the number of epithelial lesions (tumors) per 10 cm of the bladder basement membrane was significantly small in all of the groups I to L compared with the group H. The number of epithelial lesions (tumors) per 10 cm of the bladder basement membrane was significantly small in the groups J to L compared even with the group G. These results revealed that the administration of the liposome encapsulating BCG-CWS to a bladder cancer rat model decreases the number of epithelial lesions (tumors) or prevents increase in the number of epithelial lesions (tumors). As shown in the right diagram of FIG. 16, the tumor volume was small in the groups I and J compared with the groups G and H. The tumor volume was significantly small particularly in the group I compared with the group H. These results revealed that the administration of the liposome encapsulating BCG-CWS to a bladder cancer rat model decreases the tumor volume or prevents increase in the tumor volume.

These results of Examples 4(1)[1-1] to 4(2) demonstrated that the lipid membrane structure which has a particle size that permits filtration sterilization, comprises a lipid bound with a peptide consisting of a plurality of arginine residues as a constituent lipid, and encapsulates a bacterial cell component having dispersibility in a non-polar solvent can attain the treatment of cancers or the inhibition of the progression of cancers. These results also demonstrated that the lipid membrane structure which has a particle size that permits filtration sterilization, comprises a lipid bound with a peptide consisting of a plurality of arginine residues as a constituent lipid, and encapsulates a bacterial cell component having dispersibility in a non-polar solvent exerts higher anticancer effect through direct administration to cancer cells.

<Example 5> Immunostimulatory Activity (1) Isolation of Naive CD4-Positive T Cell Blood was collected from each of 4 healthy test subjects, and peripheral blood mononuclear cells were isolated using Ficoll-Paque (Pharmacia & Upjohn Company LLC). Subsequently, the cells were reacted with an FITC-labeled anti-CD8/CD45RO antibody to label naive CD4-positive T cells with FITC. Next, the FITC-labeled cells were isolated using anti-FITC magnetic beads (Miltenyi Biotec) and AutoMACS cell sorter (Miltenyi Biotec) to obtain naive CD4-positive T cells.

(2) Addition of Liposome

A *Mycobacterium Bovis bacillus* Calmette-Guerin cell-wall (BCG-CW) fraction suspended in PBS, the empty liposome of Example 1(1)[1-1], and the liposome encapsulating BCG-CWS of Example 1(1)[1-3] were each added to a medium for the naive CD4-positive T cells of Example 5(1) and used as a positive control group, a negative control group, and a test group, respectively. The amount of BCG-CW or BCG-CWS added was 1, 3, 10, and 30 μg/mL as final concentrations. Non-supplemented naive CD4-positive T cells were used as a reference group. Subsequently, these cell groups were each cultured for 1 week in a $CO_2$ incubator of 37° C. using a medium for induction of differentiation into Th1 cells or Th2 cells. In this 1-week culture period, the first 2 days were directed to culture in each medium supplemented with 20 μg/mL anti-CD3 antibody, and the remaining 5 days were directed to culture in each medium unsupplemented with the anti-CD3 antibody. The medium for induction of differentiation into Th1 cells used was an RPMI1640 medium containing 10% serum and containing 50 U/mL IL-2 (Shionogi & Co., Ltd.), 1 ng/mL IL-12 (R & D Systems, Inc.), and 5 μg/mL anti-IL-4 antibody (BD Biosciences). The medium for induction of differentiation into Th2 cells used was an RPMI1640 medium containing 10% serum and containing 50 U/mL IL-2 (Shionogi & Co., Ltd.), 1 ng/mL IL-4 (R & D Systems, Inc.), and 5 μg/mL anti-IFN-γ antibody (BD Biosciences). Then, the cells were reacted with an anti-IFN-γ antibody and an anti-IL-4 antibody, and IFN-γ-producing cells and IL-4-producing cells were detected by flow cytometry (FACSCalibur; Nippon Becton Dickinson Company Ltd.). The results about one person randomly selected from the 4 test subjects are shown in FIG. 17.

Figure 17:
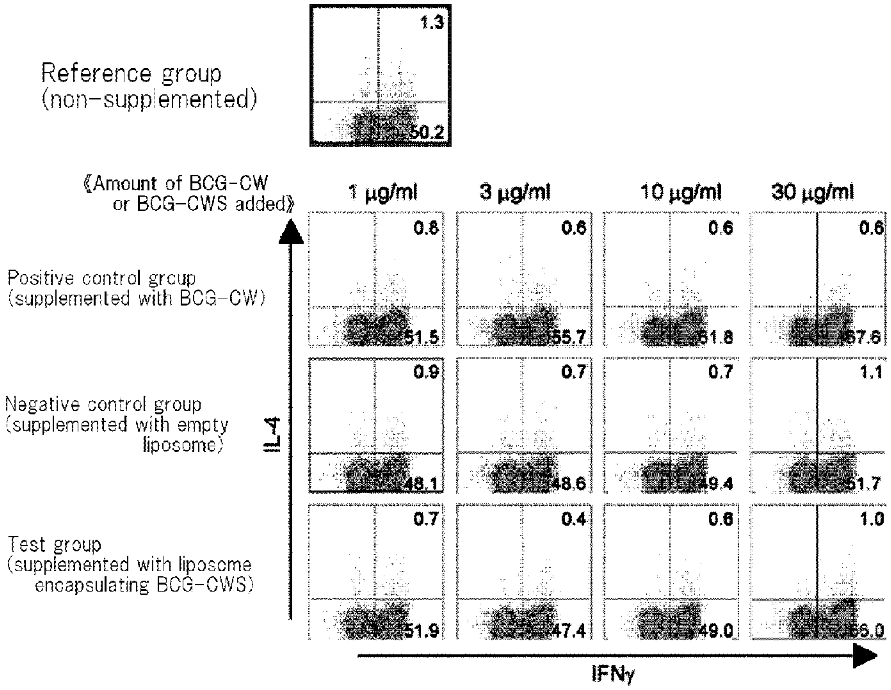
FIG. 17 is a diagram showing the relationship between the production of IFN-γ and IL-4 and the number of cells for non-supplemented naive CD4-positive T cells (reference group) and naive CD4-positive T cells supplemented with BCG-CW (positive control group), an empty liposome (negative control group), or a liposome encapsulating BCG-CWS (test group).
Figure 17:
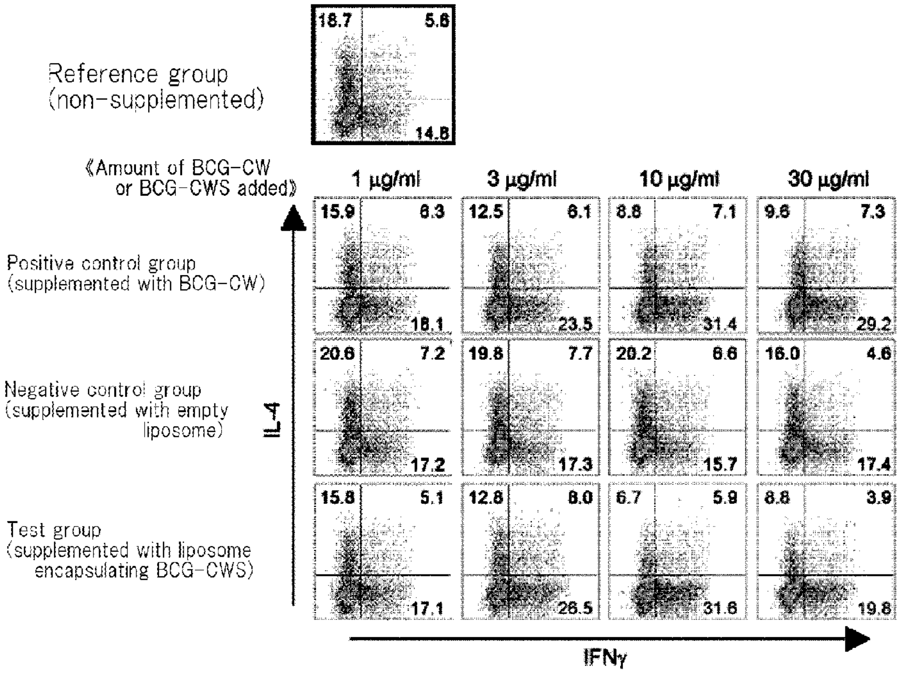

As shown in the upper diagram of FIG. 17, in the case of using the medium for induction of differentiation into Th1 cells (under the environment to induce differentiation into Th1), the number of cells producing IFN-γ and producing no IL-4 (Th1 cells) was large in the test group compared with the negative control group, regardless of the amount of BCG-CW or BCG-CWS added. Particularly, when the amount of BCG-CW or BCG-CWS added was 30 μg/mL, the number of Th1 cells in the test group was larger than that in the negative control group and the reference group and was equivalent to that in the positive control group. These results revealed that the liposome encapsulating BCG-CWS promotes the differentiation of naive CD4-positive T cells into Th1 cells under the environment to induce differentiation into Th1.

On the other hand, as shown in the lower diagram of FIG. 17, in the case of using the medium for induction of differentiation into Th2 cells (under the environment to induce differentiation into Th2), the number of cells producing no IFN-γ and producing IL-4 (Th2 cells) in the test group was smaller than that in the negative control group and the reference group and was equivalent to that in the positive control group, regardless of the amount of BCG-CW or BCG-CWS added. When the amount of BCG-CW or BCG-CWS added was 3, 10, and 30 μg/mL, the number of Th1 cells in the test group was larger than that in the negative control group and the reference group and was equivalent to that in the positive control group. These results revealed that the liposome encapsulating BCG-CWS promotes the differentiation of naive CD4-positive T cells into Th1 cells and suppresses the differentiation thereof into Th2 cells even under the environment to induce differentiation into Th2.

Next, the rate at which the naive CD4-positive T cells were converted into IFN-γ-producing cells or IL-4-producing cells (rate of conversion; %) was calculated on the basis of the flow cytometry measurement results. The rate of conversion was calculated as the ratio of IFN-γ-producing cells or IL-4-producing cells in each group when the ratio of IFN-γ-producing cells or IL-4-producing cells in the reference group was defined as 100%. Subsequently, a mean of the results about the 4 test subjects and standard deviation were determined as to the rate of conversion. The rate of conversion of the test group was subjected to a significance test (unpaired t-test) vs. the negative control group. The results are shown in FIG. 18.

Figure 18:
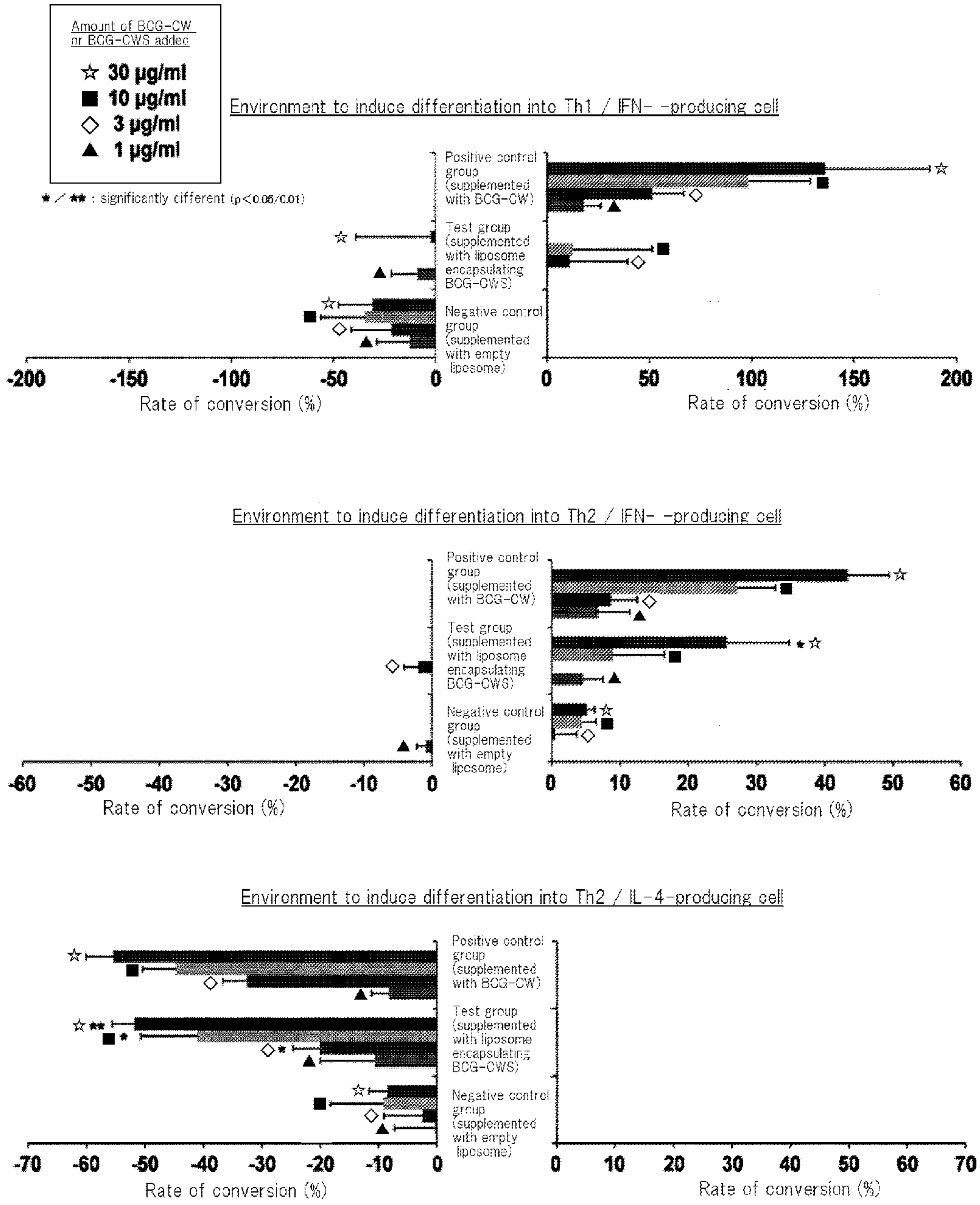
FIG. 18 is a diagram showing the rates of conversion (%) into IFN-γ-producing cells and IL-4-producing cells for naive CD4-positive T cells supplemented with BCG-CW (positive control group), a liposome encapsulating BCG-CWS (test group), or an empty liposome (negative control group).

As shown in FIG. 18, the rate of conversion into IFN-γ-producing cells in the test group tended to be large as compared with the negative control group both under the environment to induce differentiation into Th1 and under the environment to induce differentiation into Th2. Particularly, when the amount of BCG-CW or BCG-CWS added was 30 μg/mL under the environment to induce differentiation into Th2, the rate of conversion into IFN-γ-producing cells in the test group was significantly large as compared with the negative control group. When the amount of BCG-CW or BCG-CWS added was 3, 10, and 30 μg/mL, the rate of conversion into IL-4-producing cells in the test group under the environment to induce differentiation into Th2 was significantly small as compared with the negative control group. Also when the amount of BCG-CW or BCG-CWS added was 1 μg/mL, this rate of conversion tended to be small as compared with the negative control group. These results revealed that the liposome encapsulating BCG-CWS promotes the differentiation of naive CD4-positive T cells into Th1 cells both under the environment to induce differentiation into Th1 and under the environment to induce differentiation into Th2. These results also revealed that the liposome encapsulating BCG-CWS suppresses the differentiation of naive CD4-positive T cells into Th2 cells under the environment to induce differentiation into Th2.

These results of Example 5(2) demonstrated that the lipid membrane structure which has a particle size that permits filtration sterilization, comprises a lipid bound with a peptide consisting of a plurality of arginine residues as a constituent lipid, and encapsulates a bacterial cell component having dispersibility in a non-polar solvent acts on immunocytes to activate cellular immunity.

The invention claimed is:

1. A lipid membrane structure that is not a liposome, said liposome having a bacterial cell component integrally with a lipid membrane, wherein the lipid membrane structure encapsulates a bacterial cell component having dispersibility in a non-polar solvent in the form of a particle having a particle size of 95 to 135 nm and comprises a constituent lipid bound to a peptide consisting of a plurality of arginine residues, wherein the bacterial cell component is cell wall fraction (CW) or cell-wall skeleton fraction (CWS) of *Mycobacterium Bovis bacillus* Calmette-Guerin (BCG).

2. The lipid membrane structure of claim 1, wherein the non-polar solvent is pentane, diethyl ether, diisopropyl ether, or hexane.

3. The lipid membrane structure of claim 1, wherein the constituent lipid is stearic acid and the peptide bound is octaarginine.

4. A composition comprising the lipid membrane structure of claim 1.

5. The composition of claim 4 further comprising a dispersion solvent.

6. The composition of claim 5 wherein the dispersion solvent is saline or a buffer solution.

* * * * *